United States Patent
Hasegawa

(10) Patent No.: US 9,023,974 B2
(45) Date of Patent: May 5, 2015

(54) ESTER GROUP-CONTAINING TETRACARBOXYLIC ACID DIANHYDRIDE, NOVEL POLYESTERIMIDE PRECURSOR DERIVED THEREFROM, AND POLYESTERIMIDE

(75) Inventor: Masatoshi Hasegawa, Funabashi (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 352 days.

(21) Appl. No.: 12/523,856

(22) PCT Filed: Jan. 28, 2008

(86) PCT No.: PCT/JP2008/051212
§ 371 (c)(1),
(2), (4) Date: Aug. 5, 2009

(87) PCT Pub. No.: WO2008/091011
PCT Pub. Date: Jul. 31, 2008

(65) Prior Publication Data
US 2009/0306329 A1    Dec. 10, 2009

(30) Foreign Application Priority Data

Jan. 26, 2007 (JP) .................. 2007-015803

(51) Int. Cl.
*C08G 73/16* (2006.01)
*C07D 307/89* (2006.01)
*H05K 1/03* (2006.01)

(52) U.S. Cl.
CPC .............. *C07D 307/89* (2013.01); *C08G 73/16* (2013.01); *H05K 1/0346* (2013.01)

(58) Field of Classification Search
CPC ... C08L 23/0869; C08L 101/00; C08L 23/26; C08L 67/02; C08L 67/025; C08L 75/04; C08L 77/02; C08L 77/06; C08L 77/12; C08L 23/16; C08L 75/06; C08L 75/12; C08G 69/40; C08G 69/44; C08G 73/16; C07D 307/89
USPC .................................... 528/288, 289
See application file for complete search history.

(56) References Cited

U.S. PATENT DOCUMENTS

2004/0038054 A1*  2/2004  Wang et al. ............... 428/473.5
2009/0306329 A1   12/2009  Hasegawa

FOREIGN PATENT DOCUMENTS

| JP | 04-029986 | 1/1992 |
|---|---|---|
| JP | 9-258229 A | 10/1997 |
| JP | 10-070157 | 3/1998 |
| JP | 11-263785 | 9/1999 |
| JP | 2004-079826 | 3/2004 |
| JP | 2005-298623 | 10/2005 |
| JP | 2006-013419 | 1/2006 |
| JP | 2006-336011 | 12/2006 |
| WO | WO 2008/091011 A1 | 7/2008 |
| WO | WO 2010/093021 A1 | 8/2010 |

OTHER PUBLICATIONS

Numata et al. "Re-examination of the relationship between packing coefficient and thermal expansion coefficient for aromatic polyimides", Polymer, 1987,V.28,pp. 2282-2288.*
M. Hasegawa et al., "Spontaneous Molecular Orientation of Polyimides Induced by Thermal Imidization, 2, In-Plane Orientation," Macromolecules, 1996, 29, pp. 7897-7909.
K. Koseki et al., "Poly(ester imide)s Derived from Trimellitic Anhydride (3). Low CTE characteristics, thermo- and solution-processability," Polymer Preprints, Japan, vol. 53, No. 2 (2004) p. 4115.
Sek, D et al., New semiladder polymers: 1. Synthesis and properties of new poly (ester imidazopyrrolone)s, Polymer, 1998, vol. 39, No. 26, p. 7001-7008.
High Performance Polymers, 18, 697 (2006).

* cited by examiner

*Primary Examiner* — Ling Choi
*Assistant Examiner* — Gennadiy Mesh
(74) *Attorney, Agent, or Firm* — Knobbe, Martens, Olson & Bear LLP

(57) ABSTRACT

A polyimide demonstrates low coefficient of hygroscopic expansion and low water absorption coefficient when used as an insulation film. The polyimide is derived from a tetracarboxylic acid dianhydride containing ester group expressed by the general formula below, and a polyester imide precursor:

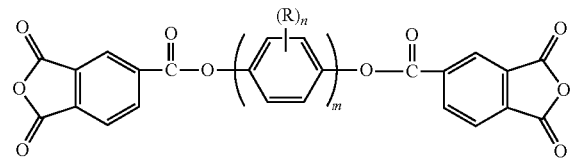

wherein R is independent and represents a straight or branched-chain alkyl group with 1 to 6 carbon atoms or straight or branched-chain alkoxyl group with 1 to 6 carbon atoms, n is an integer of 0 to 4, and m is an integer of 2 to 4, but wherein, if m =2, n is an integer of 1 to 4.

1 Claim, 30 Drawing Sheets

[Fig. 4]

| No. | cm-1 | %T | No. | cm-1 | %T | No. | cm-1 | %T |
|---|---|---|---|---|---|---|---|---|
| 1 | 3105.8 | 46.3215 | 2 | 3072.05 | 45.6976 | 3 | 2923.56 | 47.895 |
| 4 | 2010.43 | 57.0795 | 5 | 1849.4 | 27.3118 | 6 | 1779.01 | 1.55 |
| 7 | 1737.55 | 10.6447 | 8 | 1621.84 | 51.7501 | 9 | 1607.38 | 52.3399 |
| 10 | 1482.99 | 26.0448 | 11 | 1428.99 | 48.3063 | 12 | 1380.78 | 53.9497 |
| 13 | 1352.82 | 46.7807 | 14 | 1291.11 | 20.7482 | 15 | 1267 | 21.1802 |
| 16 | 1229.4 | 1.59574 | 17 | 1175.4 | 11.4934 | 18 | 1119.47 | 19.9803 |
| 19 | 1103.08 | 28.1398 | 20 | 1066.44 | 44.7099 | 21 | 926.628 | 25.3327 |
| 22 | 897.701 | 18.9207 | 23 | 862.025 | 49.6897 | 24 | 840.812 | 48.6048 |
| 25 | 805.135 | 44.3006 | 26 | 767.53 | 55.2976 | 27 | 719.318 | 14.4056 |
| 28 | 696.177 | 45.1184 | 29 | 659.536 | 60.682 | 30 | 640.251 | 61.1439 |
| 31 | 616.145 | 56.1879 | 32 | 605.539 | 56.3552 | | | |

Condition
upper 91.49   lower -6.85   depth 2.00

Peak table

Condition
upper 81.52    lower 36.48    depth 2.00

Peak table

Condition
upper 95.42   lower 24.72   depth 2.00

Peak table

| | | | | | |
|---|---|---|---|---|---|
| 1: | 3298.57( 72.0) | 2: | 2361.08( 75.9) | 3: | 1734.16( 41.7) |
| 4: | 1658.93( 47.1) | 5: | 1518.11( 42.1) | 6: | 1487.25( 47.2) |
| 7: | 1408.16( 65.0) | 8: | 1288.56( 42.3) | 9: | 1217.19( 30.6) |
| 10: | 1168.97( 51.3) | 11: | 1120.74( 53.0) | 12: | 1091.81( 58.2) |
| 13: | 1005.00( 72.0) | 14: | 920.13( 72.1) | 15: | 798.60( 64.2) |
| 16: | 744.59( 66.1) | 17: | 655.86( 67.0) | 18: | 522.76( 68.7) |
| 19: | 418.59( 51.3) | | | | |

Condition
upper 100.00   lower   0.00   depth   2.00

Peak table

| | | | | | |
|---|---|---|---|---|---|
| 1: | 3032.37( 77.9) | 2: | 2283.92( 85.4) | 3: | 1782.39( 62.0) |
| 4: | 1724.52(  9.2) | 5: | 1606.85( 72.0) | 6: | 1520.04( 37.2) |
| 7: | 1487.25( 35.3) | 8: | 1386.94( 26.7) | 9: | 1282.78( 21.0) |
| 10: | 1248.06( 28.6) | 11: | 1209.48( 10.7) | 12: | 1168.97( 25.7) |
| 13: | 1126.53( 30.6) | 14: | 1097.60( 53.3) | 15: | 1059.02( 64.7) |
| 16: | 1020.44( 82.8) | 17: | 1005.00( 76.0) | 18: | 929.77( 74.3) |
| 19: | 833.32( 72.1) | 20: | 804.39( 64.5) | 21: | 721.44( 49.0) |
| 22: | 696.37( 68.1) | 23: | 561.34( 68.3) | 24: | 530.47( 68.0) |
| 25: | 451.38( 68.2) | | | | |

Condition
upper 82.44   lower 6.65   depth 2.00

Peak table

| | | | | | |
|---|---|---|---|---|---|
| 1: | 3308.22( 50.5) | 2: | 3051.66( 52.8) | 3: | 1734.16( 17.2) |
| 4: | 1602.99( 23.0) | 5: | 1535.48( 26.2) | 6: | 1512.33( 27.1) |
| 7: | 1489.18( 27.2) | 8: | 1410.09( 37.0) | 9: | 1205.62( 13.0) |
| 10: | 1170.90( 18.0) | 11: | 1122.67( 33.3) | 12: | 1086.02( 33.8) |
| 13: | 1016.58( 53.1) | 14: | 920.13( 60.3) | 15: | 804.39( 47.3) |
| 16: | 746.52( 50.0) | 17: | 704.08( 52.8) | 18: | 655.86( 55.0) |
| 19: | 520.83( 54.0) | | | | |

Condition
upper 100.00    lower   0.00    depth   2.00

Peak table

| | | | | | |
|---|---|---|---|---|---|
| 1: | 3070.95( 81.0) | 2: | 1784.32( 60.4) | 3: | 1724.52(  6.8) |
| 4: | 1604.92( 61.2) | 5: | 1514.26( 32.2) | 6: | 1489.18( 36.1) |
| 7: | 1392.73( 30.3) | 8: | 1277.00( 11.8) | 9: | 1249.99( 26.2) |
| 10: | 1215.26(  2.8) | 11: | 1167.04( 16.8) | 12: | 1124.60( 25.2) |
| 13: | 1078.31( 46.5) | 14: | 1018.51( 62.1) | 15: | 1005.00( 71.7) |
| 16: |  929.77( 74.8) | 17: |  864.19( 72.2) | 18: |  804.39( 63.3) |
| 19: |  721.44( 47.2) | | | | |

Condition
upper 100.00   lower 30.00   depth 2.00

Peak table

| | | | | | |
|---|---|---|---|---|---|
| 1: | 3273.50( 76.9) | 2: | 2930.14( 75.0) | 3: | 1736.03( 48.3) |
| 4: | 1666.65( 47.2) | 5: | 1602.99( 53.3) | 6: | 1533.55( 53.7) |
| 7: | 1489.18( 41.2) | 8: | 1417.81( 59.0) | 9: | 1323.29( 43.5) |
| 10: | 1217.19( 35.1) | 11: | 1170.90( 37.2) | 12: | 1120.74( 41.1) |
| 13: | 1005.00( 73.6) | 14: | 896.98( 77.7) | 15: | 839.11( 73.8) |
| 16: | 798.60( 73.7) | 17: | 744.59( 76.4) | 18: | 657.79( 79.6) |
| 19: | 524.69( 91.0) | | | | |

Condition
upper 99.94   lower 8.31   depth 2.00

Peak table

| | | | | | |
|---|---|---|---|---|---|
| 1: | 3315.93( 66.7) | 2: | 3051.66( 71.6) | 3: | 2588.70( 73.0) |
| 4: | 2361.08( 76.1) | 5: | 1734.16( 23.0) | 6: | 1602.99( 38.4) |
| 7: | 1533.55( 36.1) | 8: | 1508.47( 34.7) | 9: | 1489.18( 33.6) |
| 10: | 1410.09( 49.1) | 11: | 1213.33( 16.0) | 12: | 1170.90( 23.7) |
| 13: | 1120.74( 42.1) | 14: | 1087.95( 45.0) | 15: | 1016.58( 74.5) |
| 16: | 1005.00( 73.7) | 17: | 920.13( 81.1) | 18: | 804.39( 67.0) |
| 19: | 746.52( 69.8) | 20: | 694.44( 72.0) | 21: | 655.86( 70.7) |
| 22: | 518.90( 63.6) | | | | |

Condition
upper 92.86   lower 14.24   depth 2.00

Peak table

| | | | | | |
|---|---|---|---|---|---|
| 1: | 3070.95( 80.3) | 2: | 1784.32( 68.8) | 3: | 1724.52( 28.8) |
| 4: | 1604.92( 67.8) | 5: | 1512.33( 53.5) | 6: | 1487.25( 52.5) |
| 7: | 1381.16( 51.3) | 8: | 1277.00( 36.8) | 9: | 1248.06( 44.3) |
| 10: | 1213.33( 20.8) | 11: | 1167.04( 35.5) | 12: | 1122.67( 43.1) |
| 13: | 1078.31( 54.7) | 14: | 1018.51( 62.2) | 15: | 1005.00( 64.8) |
| 16: | 929.77( 67.9) | 17: | 860.33( 68.0) | 18: | 804.39( 63.3) |
| 19: | 761.95( 73.3) | 20: | 721.44( 56.3) | 21: | 559.41( 77.2) |
| 22: | 516.97( 78.6) | | | | |

Condition
upper 95.28    lower -0.82    depth 2.00

Peak table

1:  3302.43( 45.6)   2:  3051.66( 48.0)   3:  2621.50( 63.5)
4:  1732.23( 11.7)   5:  1660.86( 21.9)   6:  1610.71( 26.5)
7:  1518.11( 12.1)   8:  1487.25( 18.8)   9:  1408.16( 31.8)
10: 1288.56( 14.5)  11:  1222.98(  7.2)  12:  1176.68( 13.5)
13: 1118.81( 11.6)  14:  1091.81( 26.6)  15:  1018.51( 67.4)
16:  920.13( 56.8)  17:   831.39( 46.7)  18:   800.53( 47.2)
19:  744.59( 48.8)  20:   657.79( 55.1)  21:   524.69( 58.1)
22:  445.60( 61.8)

Condition
upper 96.57   lower 6.56   depth 2.00

Peak table

| | | |
|---|---|---|
| 1: 3489.54( 81.6) | 2: 3069.02( 79.0) | 3: 1782.39( 54.1) |
| 4: 1722.59( 14.1) | 5: 1622.28( 70.8) | 6: 1520.04( 29.6) |
| 7: 1487.25( 41.3) | 8: 1377.30( 21.0) | 9: 1282.78( 22.9) |
| 10: 1248.06( 29.0) | 11: 1209.48( 18.1) | 12: 1178.61( 26.7) |
| 13: 1124.60( 23.6) | 14: 1095.67( 43.3) | 15: 1064.80( 60.0) |
| 16: 1022.36( 72.1) | 17: 929.77( 64.5) | 18: 854.54( 69.7) |
| 19: 831.39( 65.5) | 20: 804.39( 67.9) | 21: 773.52( 74.1) |
| 22: 721.44( 41.1) | 23: 694.44( 66.4) | 24: 561.34( 74.0) |
| 25: 532.40( 70.5) | 26: 445.60( 71.9) | |

Condition
upper 95.59    lower -3.48    depth 2.00

Peak table

| | | | | | |
|---|---|---|---|---|---|
| 1: | 3306.29( 44.1) | 2: | 3053.59( 43.8) | 3: | 2928.21( 43.6) |
| 4: | 2613.78( 59.6) | 5: | 2363.01( 65.1) | 6: | 1734.16( 6.2) |
| 7: | 1668.58( 14.1) | 8: | 1602.99( 13.2) | 9: | 1535.48( 12.3) |
| 10: | 1510.40( 11.8) | 11: | 1487.25( 16.7) | 12: | 1410.09( 19.4) |
| 13: | 1222.98( 4.8) | 14: | 1174.75( 5.2) | 15: | 1118.81( 9.1) |
| 16: | 1087.95( 16.8) | 17: | 1014.65( 46.5) | 18: | 987.64( 61.2) |
| 19: | 920.13( 53.2) | 20: | 854.54( 42.0) | 21: | 802.46( 41.1) |
| 22: | 761.95( 39.7) | 23: | 706.01( 50.0) | 24: | 659.71( 49.8) |
| 25: | 572.91( 60.3) | 26: | 522.76( 58.6) | 27: | 447.53( 62.9) |

Condition
upper  93.33    lower  -4.30    depth   2.00

Peak table

```
 1:  3489.54( 80.0)   2:  3070.95( 76.2)   3:  1784.32( 40.8)
 4:  1724.52(  4.7)   5:  1606.85( 47.3)   6:  1512.33( 15.2)
 7:  1487.25( 26.9)   8:  1385.01( 12.3)   9:  1275.06(  7.5)
10:  1211.41(  3.8)  11:  1172.83(  8.8)  12:  1120.74(  9.3)
13:  1076.38( 26.5)  14:  1018.51( 45.1)  15:   929.77( 57.7)
16:   864.19( 50.2)  17:   806.32( 58.8)  18:   761.95( 63.8)
19:   721.44( 30.2)  20:   657.79( 76.3)  21:   632.71( 75.2)
22:   609.56( 71.5)  23:   561.34( 70.0)  24:   528.54( 70.1)
25:   445.60( 75.2)
```

Condition
upper 95.48  lower 2.92  depth 2.00

Peak table

1:  3306.29( 53.7)   2:  3055.52( 55.2)   3:  2819.57( 68.8)
    4:  1732.23( 16.0)   5:  1602.99( 29.0)   6:  1535.48( 26.9)
    7:  1500.75( 21.9)   8:  1410.09( 36.3)   9:  1222.98( 10.6)
   10:  1174.75( 14.1)  11:  1118.81( 19.3)  12:  1089.88( 31.4)
   13:  1014.65( 58.3)  14:   920.13( 63.0)  15:   854.54( 53.6)
   16:   802.46( 53.1)  17:   761.95( 53.4)  18:   657.79( 60.9)
   19:   520.83( 61.9)  20:   447.53( 64.5)

Condition
upper 177.36    lower 21.51    depth 2.00

Peak table

| | | | | | |
|---|---|---|---|---|---|
| 1: | 3852.19(157.6) | 2: | 3815.54(159.0) | 3: | 3800.11(159.3) |
| 4: | 3744.17(157.9) | 5: | 3294.71(121.8) | 6: | 3030.44(120.6) |
| 7: | 2613.78(141.4) | 8: | 1917.42(153.8) | 9: | 1734.16( 58.7) |
| 10: | 1660.86( 75.5) | 11: | 1610.71( 87.0) | 12: | 1516.19( 63.0) |
| 13: | 1500.75( 70.1) | 14: | 1485.32( 58.7) | 15: | 1408.16(104.1) |
| 16: | 1286.64( 61.2) | 17: | 1217.19( 34.5) | 18: | 1170.90( 84.1) |
| 19: | 1122.67( 51.3) | 20: | 1089.88( 94.3) | 21: | 1003.07(135.8) |
| 22: | 920.13(140.4) | 23: | 891.19(138.1) | 24: | 827.54(115.3) |
| 25: | 804.39(115.4) | 26: | 746.52(136.2) | 27: | 659.71(151.5) |
| 28: | 567.12(155.4) | 29: | 522.76(149.3) | 30: | 445.60(147.7) |

Condition
upper 95.26    lower -3.99    depth 2.00

Peak table

| | | | | | |
|---|---|---|---|---|---|
| 1: | 3487.61( 80.8) | 2: | 3030.44( 75.2) | 3: | 1782.39( 51.6) |
| 4: | 1722.59( 4.3) | 5: | 1606.85( 72.8) | 6: | 1520.04( 27.5) |
| 7: | 1502.68( 23.6) | 8: | 1485.32( 19.7) | 9: | 1431.31( 69.3) |
| 10: | 1383.09( 13.2) | 11: | 1282.78( 12.9) | 12: | 1246.13( 12.5) |
| 13: | 1209.48( 5.8) | 14: | 1168.97( 17.9) | 15: | 1126.53( 13.7) |
| 16: | 1095.67( 37.8) | 17: | 1060.94( 55.7) | 18: | 1022.36( 72.3) |
| 19: | 1003.07( 68.7) | 20: | 931.70( 63.2) | 21: | 885.41( 67.3) |
| 22: | 862.26( 68.0) | 23: | 829.47( 53.6) | 24: | 806.32( 43.6) |
| 25: | 781.24( 68.6) | 26: | 721.44( 35.2) | 27: | 696.37( 66.3) |
| 28: | 605.70( 79.3) | 29: | 559.41( 74.7) | 30: | 532.40( 76.5) |

Condition
upper  88.63   lower   9.27   depth   2.00

Peak table

| | | | | | |
|---|---|---|---|---|---|
| 1: | 3308.22( 49.2) | 2: | 3032.37( 49.0) | 3: | 2928.21( 49.7) |
| 4: | 2613.78( 60.0) | 5: | 2361.08( 61.3) | 6: | 1917.42( 68.0) |
| 7: | 1732.23( 20.1) | 8: | 1662.79( 27.8) | 9: | 1604.92( 26.8) |
| 10: | 1502.68( 24.3) | 11: | 1485.32( 24.0) | 12: | 1410.09( 34.5) |
| 13: | 1217.19( 15.9) | 14: | 1170.90( 21.5) | 15: | 1122.67( 20.8) |
| 16: | 1086.02( 31.4) | 17: | 1016.58( 53.1) | 18: | 1003.07( 54.5) |
| 19: | 922.06( 56.8) | 20: | 804.39( 38.8) | 21: | 746.52( 48.7) |
| 22: | 725.30( 49.7) | 23: | 657.79( 52.4) | 24: | 563.26( 58.2) |
| 25: | 526.61( 55.8) | 26: | 449.45( 59.7) | 27: | 424.38( 61.5) |
| 28: | 410.87( 60.8) | | | | |

Condition
upper 92.42    lower 9.06    depth 2.00

Peak table

1:  3854.12( 80.7)   2:  3736.45( 80.3)   3:  3649.65( 80.9)
4:  3487.61( 81.6)   5:  3030.44( 75.2)   6:  1782.39( 53.6)
7:  1726.45( 18.4)   8:  1606.85( 60.1)   9:  1502.68( 29.7)
10: 1485.32( 32.6)  11:  1377.30( 29.4)  12:  1278.92( 25.2)
13: 1246.13( 25.9)  14:  1213.33( 16.0)  15:  1168.97( 25.8)
16: 1122.67( 26.7)  17:  1080.23( 49.7)  18:  1018.51( 62.9)
19: 1003.07( 69.8)  20:   929.77( 68.6)  21:   885.41( 67.0)
22:  854.54( 62.3)  23:   831.39( 61.5)  24:   808.25( 51.8)
25:  781.24( 70.0)  26:   761.95( 68.1)  27:   723.37( 45.0)
28:  607.63( 72.0)  29:   561.34( 68.8)  30:   526.61( 67.5)

ESTER GROUP-CONTAINING TETRACARBOXYLIC ACID DIANHYDRIDE, NOVEL POLYESTERIMIDE PRECURSOR DERIVED THEREFROM, AND POLYESTERIMIDE

This application is the U.S. National Phase under 35 U.S.C. §371 of International Application PCT/JP2008/051212, filed Jan. 28, 2008, which claims priority to Japanese Patent Application No. 2007-015803, filed Jan. 26, 2007. The International Application was published under PCT Article 21(2) in a language other than English.

TECHNICAL FIELD

The present invention relates to a novel ester group-containing tetracarboxylic acid dianhydride which is useful as materials for polyesterimide resin and other heat-resistant resins, heat-resistant hardeners for epoxy resin, etc., or resin reforming agents, as well as a novel polyesterimide precursor derived therefrom and polyesterimide.

This polyesterimide proposed by the present invention offers high glass transition temperature, low linear heat expansion coefficient, low water absorption coefficient, high modulus of elasticity and sufficient toughness, and therefore is useful as substrates for flexible print circuits (FPC), base materials for tape automation bonding (TAB), electrical insulation films or LCD substrates for various electronic devices, substrates for organic electroluminescence (EL) displays, substrates for electronic papers, and substrates for solar cells, but especially as materials for FPC and TAB substrates.

RELATED ART

Polyimide offers not only excellent heat resistance, but also various other characteristics such as chemical resistance, radiation resistance, electrical insulation property and excellent mechanical properties, etc., and is therefore used widely in FPC substrates, base materials for TAB, protection films for semiconductor elements, inter-layer insulation films for integrated circuits, and various other electronic devices. In addition to the aforementioned characteristics, polyimide offers other advantages such as ease of production, extremely high film purity, ease of modifying physical properties using various available monomers, etc., and thus its importance has been increasing in recent years.

On the other hand, the accelerating trend for lighter, thinner, shorter and smaller electronic devices is requiring increasingly greater characteristics from polyimide each year, and now the market is demanding multi-functional polyimide materials that not only offer resistance to soldering heat, but also satisfy multiple characteristics at the same time including sufficient dimensional stability of polyimide film against thermo-cycles and moisture absorption, transparency and adhesion with metal foils.

Also, the demand for polyimide is increasing dramatically in recent years for use in FPC substrates. Base materials used for FPC (flexible copper clad laminate, or FCCL) are classified into three key patterns. They are: 1) 3-layer type where polyimide film and copper foil are attached using epoxy adhesive, etc., 2) adhesive-free 2-layer type where copper foil is coated with polyimide varnish and then dried, or polyimide precursor (polyamide acid) vanish is coated and then dried/imidized, or copper layer is formed on polyimide film using deposition, sputtering, etc., and 3) pseudo 2-layer type where thermoplastic polyimide is used as an adhesive layer. In application where high dimensional stability is required of polyimide film, the 2-layer FCCL is more advantageous. Dimensional stability is required against both heat expansion and moisture absorption.

When used in FPC substrates, polyimide changes its dimensions as it is exposed to various thermo-cycles in the installation process. To minimize these dimensional changes, it is desirable that the glass transition temperature (Tg) of polyimide be higher than the temperature in the installation process and that the linear heat expansion coefficient of polyimide be made as low as possible at Tg or below. In addition, it is extremely important to control the linear heat expansion coefficient of the polyimide layer, also from the viewpoint of reducing the residual stress that generates in the 2-layer FCCL production process.

However, many types of polyimide are insoluble in organic solvents and do not melt even at Tg or above, and accordingly it is normally not easy to form/process polyimide itself. For this reason, polyimide film is generally produced by causing pyromellitic acid anhydride (PMDA) or other aromatic tetracarboxylic acid dianhydride to undergo equimolar reaction with 4,4'-oxydianiline (ODA) or other aromatic diamine in dimethyl acetoamide (DMAc) or other aprotic polar organic solvent in order to polymerize the polyimide precursor (polyamide acid) of high polymerization degree first, and then by coating a varnish thereof on copper foil and heating the copper foil at 250 to 400° C. to achieve cyclodehydration (imidization).

In this case, residual stress generates during the process of cooling the polyimide/metal substrate laminate to room temperature after the imidization reaction at high temperature, and this residual stress sometimes presents serious problems such as curling and separation of FCCL, breaking of film, and so on.

Accordingly, one effective way to reduce heat stress is to lower the heat expansion of polyimide itself, which is an insulation film. Most types of polyimide have their liner heat expansion coefficient in a range of 40 to 100 ppm/K, which is much greater than the linear heat expansion coefficients of metal foils such as copper foil whose linear heat expansion coefficient is 17 ppm/K. Accordingly, R&D efforts are underway to create low heat expansion polyimide whose linear heat expansion coefficient is approx. 20 ppm/K or less which is equivalent to copper.

Currently, the best known low heat expansion polyimide material that can be put to practical use is one produced from 3,3',4,4'-biphenyl tetracarboxylic acid dianhydride and p-phenylene diamine. This polyimide film is known to demonstrate a very low linear heat expansion coefficient of 5 to 10 ppm/K, although the specific linear heat expansion coefficient varies depending on the film thickness and production condition (refer to Non-patent Literature 1, for example). However, it does not have low water absorbency.

On the other hand, dimensional stability of polyimide is required not only against thermo-cycles, but also against moisture absorption. Conventional types of polyimide absorb moisture by as much as 2 to 3 percent by weight. In the case of high-density wirings and multi-layer wirings, moisture absorption by insulation layers can cause problems such as shifting of circuit positions due to dimensional change. In particular, it can cause separation of conductor layers, corrosion at the interface of polyimide/conductor, migration of ions, insulation failure, and drop in other electrical characteristics. Accordingly, moisture absorption has presented a challenge that needs to be improved. To address this problem, it is desirable to lower as much as possible the coefficient of hygroscopic expansion of polyimide, which is used for insulation films, and to this end it is required that the water absorption coefficient of polyimide be kept low.

As a molecular design to lower the water absorbency of polyimide, it has been reported effective to introduce, for example, ester bond to the polyimide skeleton using an ester group-containing tetracarboxylic acid dianhydride expressed by formula (4) below which is derived from trimellitic acid anhydride and hydroquinone (refer to Non-pateint Literature 2,for example).

[Chemical 1]

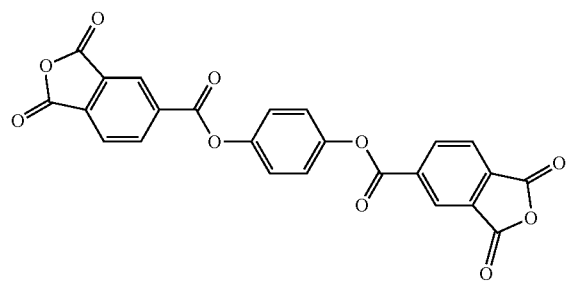

(4)

In addition to the above, several other types of polyimide are also reported which are derived from tetracarboxylic acid dianhydrides containing ester group having different structures (refer to Japanese Patent Laid-open Nos. Hei 10-70157, Hei 11-263785, 2005-298623 and 2006-13419, for example).

However, it is not easy, in terms of molecular design, to obtain a heat-resistant insulation material offering the required low linear heat expansion coefficient (such as 20 ppm/K or less as a target), low water absorption coefficient (such as 0.8% or less), sufficient film toughness, resistance to soldering heat, and adhesion with metal foils such as copper foil, among others, while retaining polymerization reactivity and film forming/processing property, and practical materials are still not known at the present which offer the physical properties required of base materials for FPC and TAB, electrical insulation films or LCD substrates for various electronic devices, substrates for organic electroluminescence (EL) displays, substrates for electronic papers, and substrates for solar cells, especially of materials for FPC and TAB substrates.

Non-patent Literature 1: Macromolecules, 29, 7897 (1996)
Non-patent Literature 2: Proceedings of Symposium on Macromolecules, 53, 4115 (2004)
Patent Literature 3: Japanese Patent Laid-open No. Hei 10-70157
Patent Literature 4: Japanese Patent Laid-open No. Hei 11-263785
Patent Literature 5: Japanese Patent Laid-open No. 2005-298623
Patent Literature 6: Japanese Patent Laid-open No. 2006-13419

SUMMARY OF THE INVENTION

Problems to be Solved by the Invention

The object of the present invention is to provide a novel polyesterimide offering high glass transition temperature, low linear heat expansion coefficient equivalent to metal foils, extremely low water absorption coefficient, high modulus of elasticity, sufficient toughness and sufficient adhesion with metal foils, as well as a novel polyesterimide precursor being a precursor of such polyesterimide, and also to provide a novel ester group-containing tetracarboxylic acid dianhydride which is used as a material to achieve the foregoing.

Means for Solving the Problems

In light of the aforementioned condition surrounding polyimide resin, the inventors conducted a series of earnest studies and consequently found that the aforementioned problems, such as achieving a lower water absorption coefficient while retaining the target physical properties, can be solved by introducing p-biphenylene group, p-terphenylene group, p-quarterphenylene group, etc. (hereinafter collectively referred to as "p-polyphenylene group") having further aromatic rings, in place of the phenylene group at the center, according to the aforementioned formula (4), and that the aforementioned problems, such as achieving a lower water absorption coefficient, can also be solved by introducing a hydrophobic substituent such as alkyl group onto the polyphenylene group. However, we do not yet know any tetracarboxylic acid dianhydride where such p-polyphenylene group is connected to a phthalic acid anhydride residue using an ester group, or any polyesterimide precursor or polyesterimide derived using such tetracarboxylic acid dianhydride.

The inventors completed the present invention after finding that a polyesterimide film expressed by general formula (3) below would provide an extremely useful material in the aforementioned field of industrial application, where such polyesterimide film is formed by obtaining varnish of a polyesterimide precursor expressed by general formula (2) below which in turn is obtained from an ester group-containing tetracarboxylic acid dianhydride expressed by general formula (1) below and a diamine, and then coating and drying this varnish of polyesterimide precursor on a conductive substrate such as copper foil, and finally imidizing the obtained film either thermally or using a cyclodehydration reagent, etc.

In other words, the present invention provides an ester group-containing tetracarboxylic acid dianhydride as expressed by general formula (1) below:

[Chemical 2]

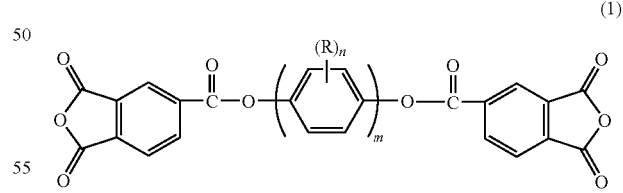

(1)

In the formula, each R is independent and represents a straight or branched-chain alkyl group with 1 to 6 carbon atoms or straight or branched-chain alkoxyl group with 1 to 6 carbon atoms, n is an integer of 0 to 4, and m is an integer of 2 to 4, with the proviso that if m=2, n is an integer of 1 to 4.

Also, the present invention provides a polyesterimide precursor having a repeating unit, expressed by general formula (2) and obtained from an ester group-containing tetracarboxylic acid dianhydride and a diamine:

[Chemical 3]

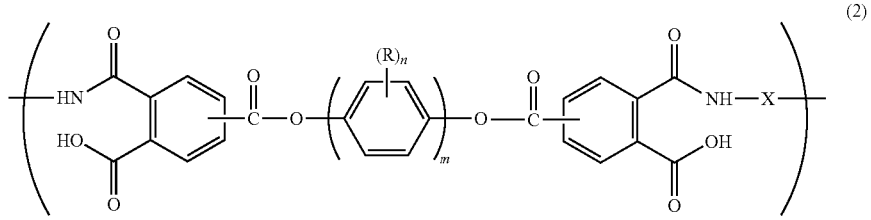

(2)

In the formula, R, n and m represent the corresponding items in general formula (1), respectively, and X represents a bivalent aromatic group and/or aliphatic group, where the ester group bonds in the meta- or para-position with respect to the amide bond. Further, the present invention provides a polyesterimide having a repeating unit, expressed by general formula (3) and obtained by imidizing the aforementioned polyesterimide precursor either thermally or using a cyclodehydration reagent, etc.:

[Chemical 4]

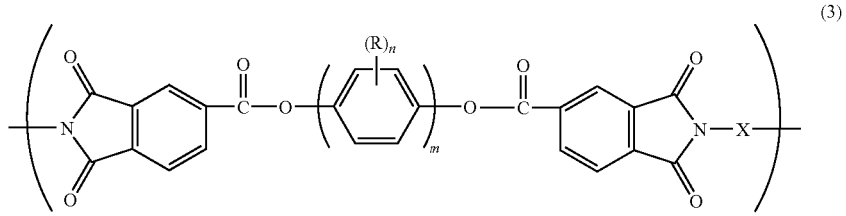

(3)

In the formula, R, n and m represent the corresponding items in general formula (1), respectively, and X represents a bivalent aromatic group and/or aliphatic group.

Effects of the Invention

The present invention provides a novel ester group-containing tetracarboxylic acid dianhydride where a phthalic acid anhydride residue is ester-bonded in the para-position of a polyphenylene group that can have a hydrophobic substituent such as alkyl group. The present invention also provides a polyesterimide precursor and polyesterimide obtained by such ester group-containing tetracarboxylic acid dianhydride and a diamine. Such polyesterimide conforming to the present invention offers high glass transition temperature, low linear heat expansion coefficient equivalent to metal foils, extremely low water absorption coefficient, high modulus of elasticity, sufficient toughness and sufficient adhesion with metal foils, and is therefore useful as base materials for FPC and TAB, electrical insulation films or LCD substrates for various electronic devices, substrates for organic EL displays, substrates for electronic papers, and substrates for solar cells, but especially as base materials for FPC and TAB.

BEST MODE FOR CARRYING OUT THE INVENTION

Figure 1:
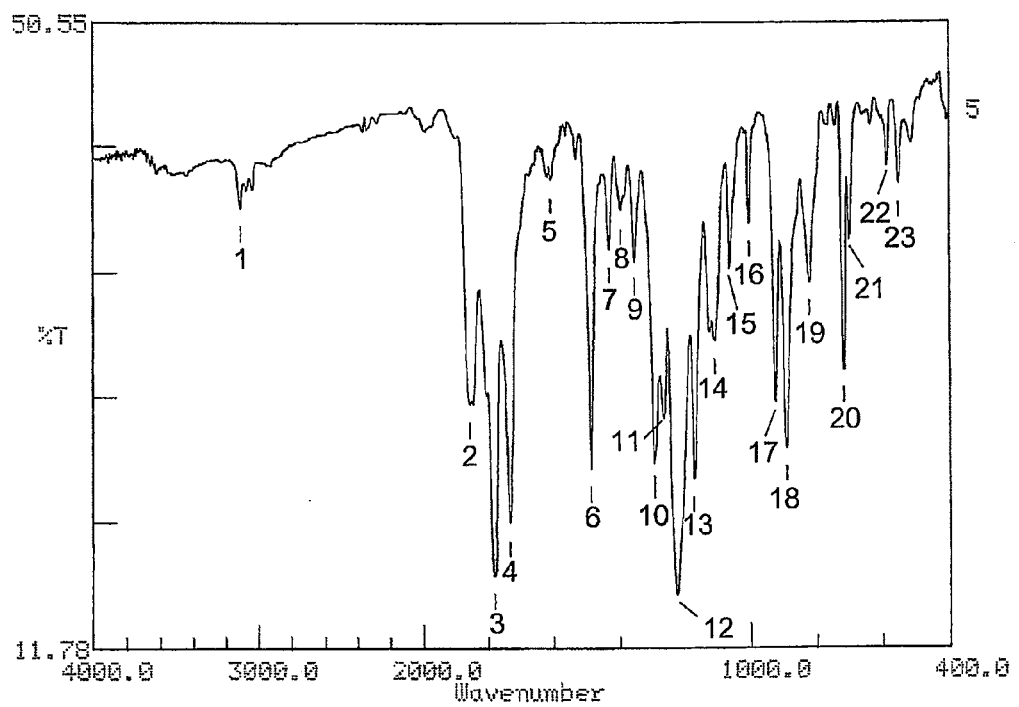
[FIG. 1] Infrared absorption spectrum of the ester group-containing tetracarboxylic acid dianhydride described in Example 1.

Varnish of a polyesterimide precursor conforming to the present invention can be coated and dried on a metal foil such as copper foil and then imidized to obtain a laminate of metal layer and polyesterimide resin layer. Furthermore, the metal layer can be etched to create a desired circuit using an etching solution such as aqueous solution of ferric chloride in order to produce an adhesive-free FPC substrate.

To apply a polyesterimide conforming to the present invention as base materials for FPC or TAB, the linear heat expansion coefficient of the obtained polyesterimide film is preferably 30 ppm/K or less, or more preferably be 20 ppm/K or less. Also, the water absorption coefficient is preferably 1.5% or less, or more preferably be 1.0% or less. The glass transition temperature is preferably 300° C. or above, or more preferably be 350° C. or above, from the viewpoint of resistance to soldering heat. Also, if the 5% weight loss temperature is 430° C. or above, no serious problems will occur. The modulus of elasticity of polyesterimide film is not specifically limited, but it is desirably 4 GPa or more, or more desirably 5 GPa or more, from the viewpoint of cost, or specifically because a thinner polyimide film can be designed when the modulus of elasticity is higher. As an indicator for film flexibility, any film which maintains breaking resistance in a 180° bending test can be applied to the aforementioned industrial field. However, it is preferable for the film to have greater breaking elongation because the greater the breaking elongation, the wider the scope of application becomes.

Also, additives such as oxidization stabilizers, fillers, adhesion promoters, silane coupling agents, photosensitizers, photopolymerization initiators, sensitizers, end capping agents and cross-bridging agents can be added, as necessary, to the polyesterimide or its precursor conforming to the present invention.

In terms of a molecular design to reduce the heat expansion of polyimide, it is generally known that it is required that the main chain skeleton be made as straight and rigid as possible in order to prevent various conformations caused by internal rotation. On the other hand, however, such main chain skeleton may reduce the entanglement of polymer chains and consequently make the film brittle. Also, introduction to the polyimide skeleton of a flexuous structure unit such as ether bond by an excessive amount prevents expression of low heat expansion characteristics, although it contributes significantly to the improvement of film toughness.

Accordingly, the present invention uses, as a tetracarboxylic acid dianhydride, a p-polyphenylene group that can have a hydrophobic substituent such as alkyl group, in order to make the main chain skeleton as straight and rigid as possible. The ester bond with an acid dianhydride group has a higher internal rotation barrier than the ether bond and therefore prevents conformation change relatively more effectively, and consequently the ester bond behaves as a rigid structure unit. By using this tetracarboxylic acid dianhydride as the material for polyimide, the main chain of polyimide is expected to have a certain level of flexibility and thus provide a flexible film.

Also, the ester bond has a lower polarizability per unit volume than the amide bond or imide bond, and thus introduction of the ester bond to polyimide is also advantageous to lowering the water absorption coefficient.

Accordingly, a novel ester group-containing tetracarboxylic acid dianhydride which conforms to the present invention is expressed by general formula (1) below:

[Chemical 5]

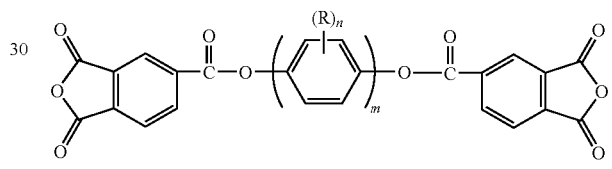

(1)

In the formula, each R is independent and represents a straight or branched-chain alkyl group with 1 to 6 carbon atoms or straight or branched-chain alkoxyl group with 1 to 6 carbon atoms, n is an integer of 0 to 4, and m is an integer of 2 to 4, with the proviso that if m=2, n is an integer of 1 to 4.

Specific examples of the straight or branched-chain alkyl group with 1 to 6 carbon atoms include methyl group, ethyl group, n-propyl group, isopropyl group, n-butyl group, t-butyl group, pentyl group, 2-methylpentyl group, and hexyl group, among others.

Also, specific examples of the straight or branched-chain alkoxyl group with 1 to 6 carbon atoms include methoxy group, ethoxy group, n-propoxy group, isopropoxy group, n-butoxy group, t-butoxy group, pentoxy group, 2-methylpentoxy group, and hexyloxy group, among others.

An ester group-containing tetracarboxylic acid dianhydride which conforms to the present invention and is expressed by general formula (1), can be produced by means of esterification reaction using a diol, or specifically a p-polyphenylene diol expressed by general formula (5) below, as well as a trimellitic acid:

[Chemical 6]

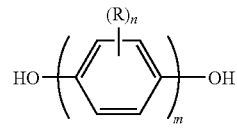

(5)

In the formula, R, n and m represent the corresponding items in general formula (1), respectively. Specific examples of such diol are given below.

Diols where m=2, such as the following:
3,3'-dimethyl-biphenyl-4,4'-diol;

[Chemical 7]

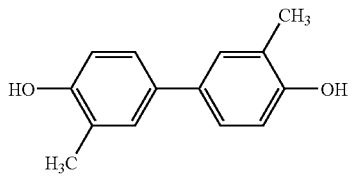
(6)

3,3'-diethyl-biphenyl-4,4'-diol;
3,3'-diisopropyl-biphenyl-4,4'-diol;
3,3',5,5'-tetramethyl-biphenyl-4,4'-diol;

[Chemical 8]

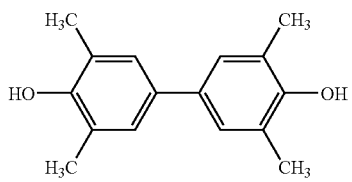
(7)

3,3',6,6'-tetramethyl-biphenyl-4,4'-diol;
2,2',3,3',5,5'-hexamethyl-biphenyl-4,4'-diol;

[Chemical 9]

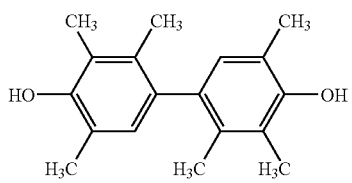
(8)

3,3'-dimethyl-5,5'-di-t-butyl-biphenyl-4,4'-diol;

[Chemical 10]

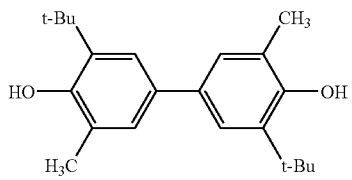
(9)

3,3'-dimethoxy-biphenyl-4,4'-diol;
3,3'-diethoxy-biphenyl-4,4'-diol;
3,3'-dipropoxy-biphenyl-4,4'-diol;
3,3',6,6'-tetramethoxy-biphenyl-4,4'-diol;

Diols where m=3, such as the following:
4,4''-dihydroxy-p-terphenyl;

[Chemical 11]

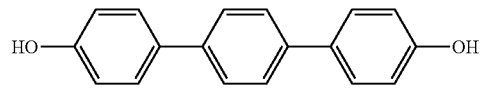
(10)

4,4''-dihydroxy-3-methyl-p-terphenyl;

[Chemical 12]

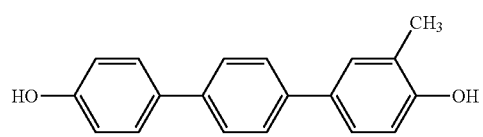
(11)

4,4''-dihydroxy-3-ethyl-p-terphenyl;
4,4''-dihydroxy-3-n-propyl-p-terphenyl;
4,4''-dihydroxy-3-isopropyl-p-terphenyl;

[Chemical 13]

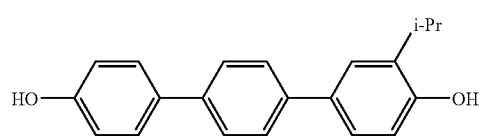
(12)

4,4''-dihydroxy-3,5-dimethyl-p-terphenyl;
4,4''-dihydroxy-3,3''-dimethyl-p-terphenyl;
4,4''-dihydroxy-3-methoxy-p-terphenyl;

[Chemical 14]

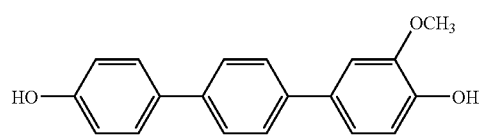
(13)

4,4''-dihydroxy-3-ethoxy-p-terphenyl;
4,4''-dihydroxy-3-n-propoxy-p-terphenyl;
4,4''-dihydroxy-3,3''-dimethoxy-p-terphenyl;
4,4''-dihydroxy-3,5-dimethoxy-p-terphenyl;
Diols where m=4, such as the following:
4,4'''-dihydroxy-p-quarterphenyl;

[Chemical 15]

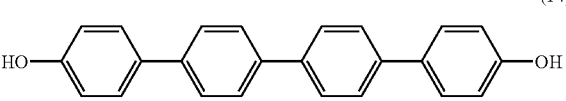
(14)

4,4'''-dihydroxy-3-methyl-p-quarterphenyl;
4,4'''-dihydroxy-3-ethyl-p-quarterphenyl;
4,4'''-dihydroxy-3-n-propyl-p-quarterphenyl;

4,4'''-dihydroxy-3,5-dimethyl-p-quarterphenyl;
4,4'''-dihydroxy-3,3'''-dimethyl-p-quarterphenyl;

[Chemical 16]

(15)

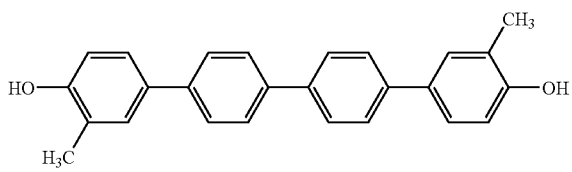

4,4'''-dihydroxy-3,3'''-diethyl-p-quarterphenyl;
4,4'''-dihydroxy-3,3'''-di-n-propyl-p-quarterphenyl;
4,4'''-dihydroxy-3,3'''-diisopropyl-p-quarterphenyl;
4,4'''-dihydroxy-3,3'''-dimethoxy-p-quarterphenyl;
4,4'''-dihydroxy-3,3'''-diethoxy-p-quarterphenyl;
4,4'''-dihydroxy-3,3'''-di-n-propoxy-p-quarterphenyl;
4,4'''-dihydroxy-3,3'''-diisopropoxy-p-quarterphenyl.

Such p-polyphenylene diols, as well as their production methods, are disclosed, for example, in Japanese Patent Laid-open Nos. 2002-308808, 2005-145820 and 2005-247809, among others.

Also, specific examples of the trimellitic acid include trimellitic acid anhydride, trimellitic acid anhydride chloride, and trimellitic acid chloride, among others.

Accordingly, tetracarboxylic acid dianhydrides containing ester group shown in the specific examples below can be used favorably as an ester group-containing tetracarboxylic acid dianhydride which conforms to the present invention and is expressed by general formula (1), from the viewpoints of ease of synthesizing a material diol, availability and costs of materials used in diol synthesis, solubility in a solvent of diol or its derivative, and the like. It should be noted, however, that the present invention is not at all limited to these examples.

(16)

[Chemical 17]

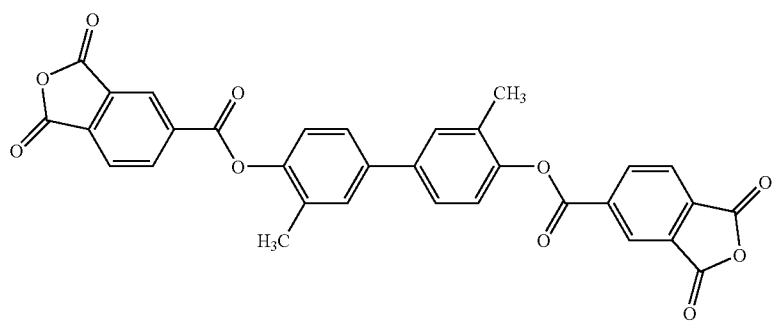

(17)

[Chemical 18]

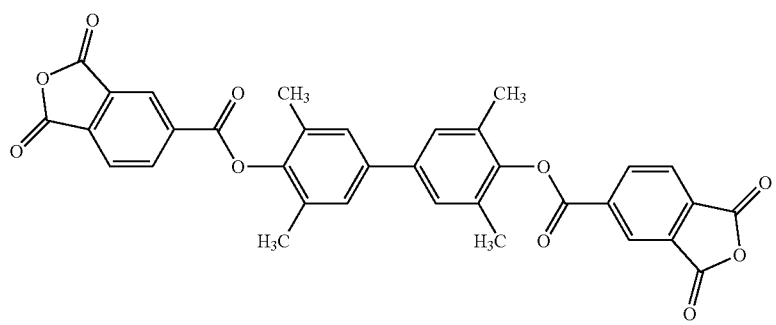

(18)

[Chemical 19]

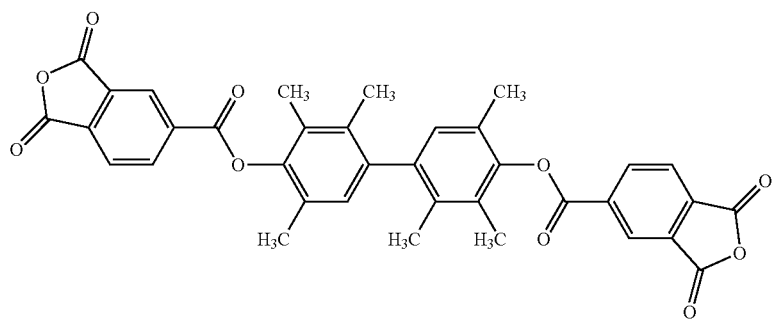

-continued
[Chemical 20]
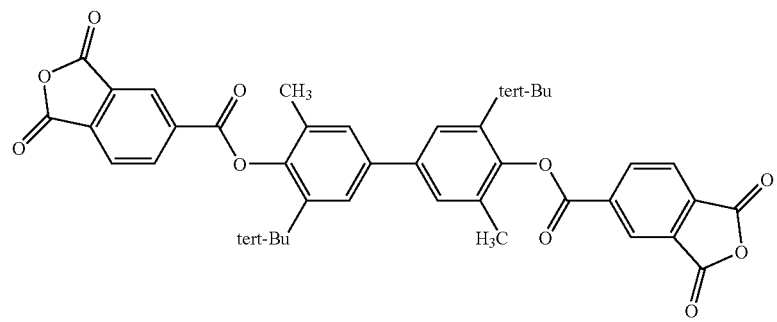
(19)
[Chemical 21]
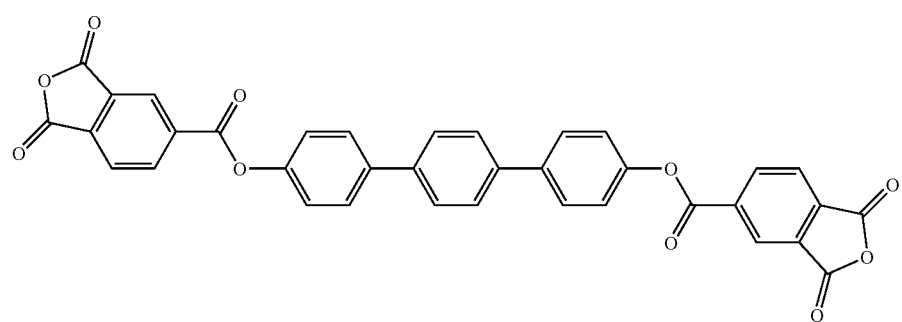
(20)
[Chemical 22]
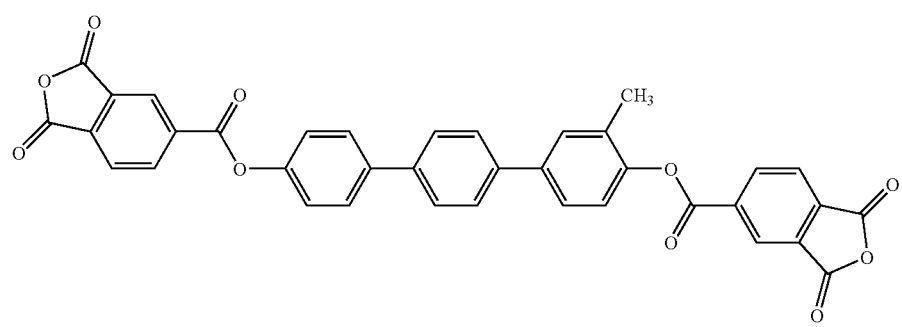
(21)
[Chemical 23]
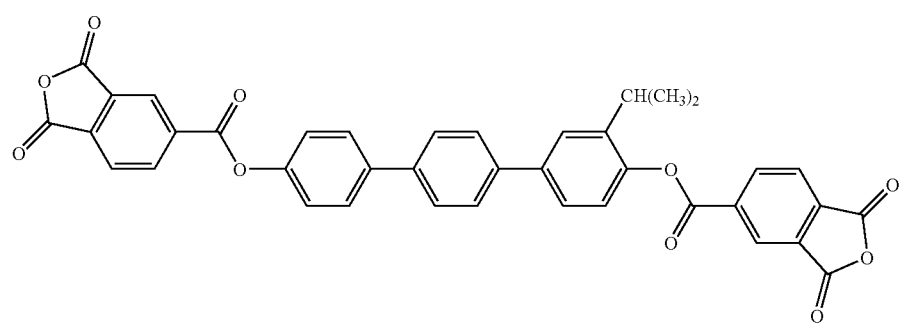
(22)

[Chemical 24]

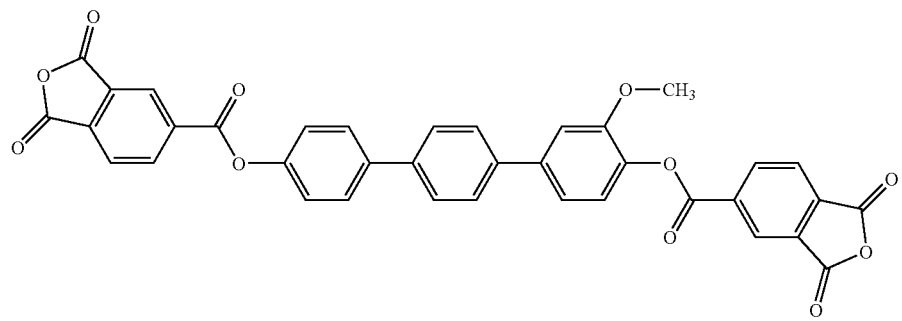

(23)

[Chemical 25]

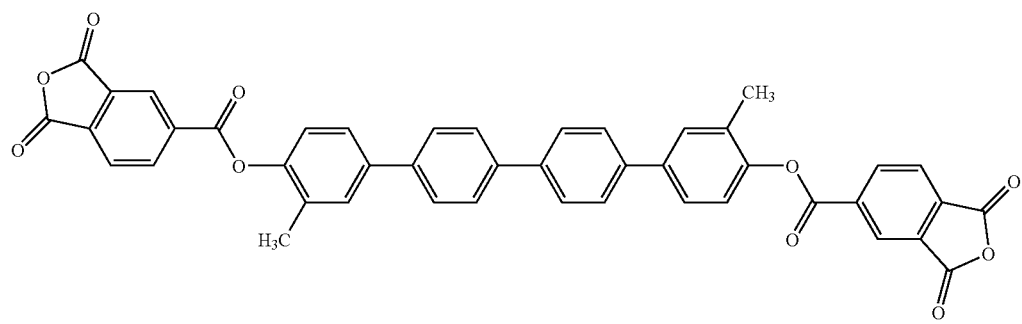

(24)

In addition, an ester group-containing tetracarboxylic acid dianhydride which conforms to the present invention and is expressed by general formula (1) does not contain any fluorine substituent. If a fluorine substituent of low polarizability is contained, any polyimide made using such fluorine substituent would be effective in lowering the water absorption coefficient, but the glass transition temperature and adhesion with metal foils may drop due to lower intermolecular force. Furthermore, such polyimide is also disadvantageous in terms of production cost. On the other hand, an ester group-containing tetracarboxylic acid dianhydride which conforms to the present invention and is expressed by general formula (1) does not contain any fluorine group and therefore by using it as the material for polyimide, a heat-resistant insulation material not heretofore available, because it offers low water absorbency and other required characteristics, can be produced at low cost.

Furthermore, one feature of tetracarboxylic acid dianhydride which conforms to the present invention and is expressed by general formula (1) is that its molecule has two to four polyphenylene groups behaving as hydrophobic groups, as well as two ester groups connecting the polyphenylene groups to phthalic acid anhydride residues, and that these groups are all connected by para-bond. This way, it is possible to simultaneously achieve extremely low water absorption coefficient, low linear heat expansion coefficient equivalent to metal foils, and high modulus of elasticity. It is not desirable to introduce to such tetracarboxylic acid dianhydride any meta-bond, ortho-bond or other bond of bent structure, because it can significantly reduce the straightness of the main polymer chain and thus prevent the achievement of low linear heat expansion coefficient.

Meanwhile, the effect of the substituent R is discussed. No major problem is anticipated when the polyphenylene diol expressed by general formula (5), which is used as the material for producing a tetracarboxylic acid dianhydride conforming to the present invention, contains no substituent R, or specifically when the polyphenylene diol is constituted entirely by hydrogen atoms. However, solubility of the diol in a solvent can be improved by introducing a bulky hydrophobic substituent such as alkyl group or alkoxyl group. Accordingly, it is advantageous to introduce a substituent into the diol because it expands the choice of solvents that can be used in the esterification reaction with trimellitic acid when synthesizing a tetracarboxylic acid dianhydride conforming to the present invention. Furthermore, the effect of such substituent increases the polymerization-solvent solubility of the monomer of such tetracarboxylic acid dianhydride and resulting polyesterimide precursor when a polyesterimide precursor is polymerized from an ester group-containing tetracarboxylic acid dianhydride which is obtained through esterification reaction and conforms to the present invention, as well as from a diamine. As a result, the polymerization reaction progresses quickly, while at the same time the resulting polyesterimide precursor does not precipitate easily, and consequently the degree of polymerization of the polyesterimide precursor tends to increase, which is an advantage.

Another effect, as a different aspect of the substituent R, is that while no major problem is anticipated when an ester group-containing tetracarboxylic acid dianhydride which conforms to the present invention does not contain any substituent R in its molecule, introduction of an appropriate substituent adds appropriate disturbance to the packing between polymer chains in the resulting polyesterimide and thereby prevents crystallization of film. As a result, film toughness may be improved while the required characteristics are maintained, which is desirable.

At this time, introducing as the substituent R a highly bulky substituent, such as phenyl group, is not desirable because it can significantly reduce the characteristics required of polyesterimide. Accordingly, favorable substituents include a straight or branched-chain alkyl group with 1 to 6 carbon atoms or straight or branched-chain alkoxyl group with 1 to 6 carbon atoms. In particular, a methyl group or methoxy group is more preferable, and a methyl group is even more preferable from the viewpoint of cost, etc.

Next, the method for producing an ester group-containing tetracarboxylic acid dianhydride which conforms to the present invention and is expressed by general formula (1) is not specifically limited, and any known method can be applied as deemed appropriate. As an example, the following explains a method for producing an ester group-containing tetracarboxylic acid dianhydride as expressed by formula (21) above.

First, a 4,4"-dihydroxy-3-methyl-p-terphenyl (hereinafter referred to as "DHTP-M") expressed by formula (11) above is used as the material diol and caused to undergo esterification reaction with a trimellitic acid anhydride.

Specific methods that can be used here include the following, for example: method to cause direct dehydration reaction at high temperature using the hydroxy group in the DHTP-M and carboxyl group in the trimellitic acid anhydride; method to achieve dehydration condensation using a dehydration reagent such as dicyclohexyl carbodiimide, etc.; method to diacetate a diol (DHTP-M) and then cause the resulting diol diacetate to react with a trimellitic acid anhydride at high temperature to achieve deacetylation and esterification (ester exchange method); method to convert the carboxyl group in the trimellitic acid anhydrate to an acid halide and then cause it to react with a diol in the presence of a deoxidization agent (base) (acid halide method); and method to activate the carboxyl group in the trimellitic acid anhydrate using a mixture of tosyl chloride/N,N-dimethyl formamide/pyridine and thereby achieve esterification. Of the aforementioned methods, the ester exchange method and acid halide method can be applied favorably from the viewpoint of economy and reactivity.

Next, a detailed explanation is given regarding an example of how an ester group-containing tetracarboxylic acid dianhydride as expressed by formula (21) and conforming to the present invention, can be synthesized using the acid halide method. First, a trimetric acid anhydride chloride (A mol) is dissolved in a solvent and the container is tightly sealed with a septum cap. Into this solution, a solvent in which DHTP-M (0.5×A mol) and an appropriate amount of a base (deoxidization agent) are dissolved is slowly dripped using a syringe or drip funnel. When the entire solution has been dripped, the reaction mixture is agitated for 24 hours. If the solubility of the target substance in the solvent used for synthesis is high, first the produced hydrochloride is filtered out from the reaction mixture, and then the filtrate is distilled away by means of solvent elimination using an evaporator, followed by vacuum-drying for 24 hours at 100 to 200° C., to obtain a crude product in powder form. If the solubility of the target substance is low, the mixture of the target substance and hydrochloride is filtered out, and this mixture is washed with an ample amount of water to dissolve and eliminate only hydrochloride. Next, the crude product is partially hydrolyzed through a partial washing process, which is then vacuum-dried at 100 to 200° C. and cyclized. The obtained crude product is recrystallized using an appropriate solvent, after which the recrystallized product is washed, heated and vacuum-dried to obtain an ester group-containing tetracarboxylic acid dianhydride of high purity, expressed by formula (21), which can be used in polymerization.

As for the solvent that can be used for this esterification reaction, any solvent can be used as long as it does not inhibit the reaction. However, favorable solvents include: tetrahydrofuran, 1,4-dioxane, picoline, pyridine, acetone, chloroform, toluene, xylene, dichloromethane, 1,2-dichloroethane, N-methyl-2-pyrrolidone, N,N-dimethylacetoamide, N,N-diethylacetoamide, N,N-dimethylformamide, hexamethylphosphoramide, dimethylsulfoxide, γ-butyrolactone, 1,3-dimethyl-2-imidazolidinone, 1,2-dimethoxyethane-bis (2-methoxyethyl) ether and other aprotic solvents; and phenol, o-cresol, m-cresol, p-cresol, o-chlorophenol, m-chlorophenol, p-chlorophenol and other protic solvents. In addition, these solvents can be used alone or two or more of them can be combined. Among others, tetrahydrofuran and 1,4-dioxane can be used favorably from the viewpoints of solubility of the reaction regent and ease of distillation.

The aforementioned esterification reaction is normally achieved at temperatures in a range of −10 to 50° C., or more preferably in a range of 0 to 30° C. If the reaction temperature is higher than 50° C., partial side reaction may occur to reduce the yield, which is not desirable.

The reaction to obtain an ester group-containing tetracarboxylic acid dianhydride is normally achieved in a solute concentration range of 5 to 50 percent by weight. When the control of side reaction and process of filtering the precipitate are considered, this reaction is achieved preferably in a solute concentration range of 10 to 40 percent by weight.

The deoxidization agent used in the reaction is not specifically limited and any substance can be used as long as it can act as a deoxidization agent. However, pyridine, triethyl amine, N,N-dimethyl aniline and other organic tertiary amines, as well as potassium carbonate, sodium hydroxide and other inorganic bases, are used.

If pyridine is used as the deoxidization agent, the precipitate produced by the reaction contains water-soluble pyridine hydrochloride. If tetrahydrofuran is used as the solvent, for example, pyridine hydrochloride hardly dissolves in this solvent and therefore hydrochloride can be separated virtually completely only by filtering the reaction solution. Normally when the solubility of the target substance is high, the target substance is dissolved in the filtrate, and accordingly the target substance can be obtained at high yield and with sufficiently high purity only by distilling the solvent away from the filtrate and then causing recrystallization using an appropriate solvent. To separate and eliminate a trace amount of chlorine content, it is also possible to dissolve the target substance again in chloroform, ethyl acetate, etc., and water-wash the organic layer using a separating funnel, or simply wash the precipitate thoroughly with water. Whether hydrochloride has been eliminated can be determined easily based on whether or not white precipitate of silver chloride is produced when 1% aqueous solution of silver nitrate is used as a washing solution. During water-washing, the ester group-containing tetracarboxylic acid dianhydride is partially hydrolyzed and changes to dicarboxylic acid. However, this dicarboxylic acid produced by partial hydrolysis can be easily cyclodehydrated back to an acid anhydrate through vacuum-drying at 80 to 250° C., or preferably at 120 to 200° C. A processing method using an organic acid anhydride can also be applied. In this case, organic acid anhydrides that can be used include acetic acid anhydride, propionic acid anhydride, maleic acid anhydride, phthalic acid anhydride, etc., among which acetic acid anhydride can be used favorably in that it can be removed easily.

Next, another aspect of the present invention is explained. To be specific, an ester group-containing tetracarboxylic acid dianhydride expressed by general formula (1) above is used as a monomer and combined with various diamines by means of polymerization reaction to obtain a novel polyesterimide precursor. Then, this polyesterimide precursor can be imidized to obtain a novel polyesterimide which is extremely useful in industrial applications. Because of the reactivity, rigidity and hydrophobicity of such ester group-containing tetracarboxylic acid dianhydride, as well as its structural advantages such as appropriate bulkiness of the substituent, a material offering physical properties that were heretofore unachievable by conventional materials, such as low linear heat expansion coefficient, high modulus of elasticity, extremely low water absorption coefficient, high glass transition temperature, sufficient film toughness and adhesion with metal foils, can be obtained as an imide resin produced from such ester group-containing tetracarboxylic acid dianhydride.

Accordingly, a novel polyesterimide precursor, which is another aspect of the present invention, can be obtained by using an ester group-containing tetracarboxylic acid dianhydride expressed by general formula (1) above and by causing it to react with a diamine.

Normally, the polymerization reactivity of tetracarboxylic acid dianhydride and diamine has significant impact on the toughness of the polyesterimide film finally achieved from the reaction. If the polymerization reactivity is not sufficiently high, a high polymer cannot be obtained and consequently the entanglement of polymer chains becomes weak, which may cause the polyesterimide film to become brittle. This is not a concern with an ester group-containing tetracarboxylic acid dianhydride which conforms to the present invention, because it has high polymerization reactivity to diamines.

By the way, the diamine, which is another material used in the polymerization of a polyesterimide precursor conforming to the present invention, is not specifically limited. If a diamine component having an extremely rigid structure is used, however, the linear heat expansion coefficient of the resulting polyesterimide film conforming to the present invention may become lower than the linear heat expansion coefficients of copper foil and other metal foils. In this case, a flexuous monomer such as 4,4'-oxydianiline can be added by an appropriate amount, as a copolymerization component, in order to perfectly match the linear heat expansion coefficient of the polyesterimide film with that of a desired metal foil, thereby preventing warping of the insulation film/metal foil laminate. Addition of such flexuous monomer also improves the toughness of the polyesterimide film to a significant degree.

The method for producing a novel polyesterimide precursor, which is another aspect of the present invention, is not specifically limited and any known method can be applied as deemed appropriate. To be specific, it can be obtained by the following method, for example. First, a diamine is dissolved in a polymerization solvent, and an ester group-containing tetracarboxylic acid dianhydride which conforms to the present invention and exists in powder form, for example, is gradually added to the obtained solution by a mol amount virtually equal to that of the diamine, after which a mechanical stirrer is used to agitate the mixture for 0.5 to 150 hours, or preferably 1 to 48 hours, at temperatures in a range of 0 to 100° C., or preferably in a range of 20 to 60° C. At this time, the concentration of the monomer is normally adjusted to a range of 5 to 50 percent by weight, or preferably to a range of 10 to 40 percent by weight. By achieving polymerization at a monomer concentration in these ranges, a uniform polyesterimide precursor solution of high polymerization degree can be obtained. If the polymerization degree of the polyesterimide precursor becomes too high and agitation of the polymerization solution becomes difficult, the solution can be diluted using the same solvent as deemed appropriate.

From the viewpoint of toughness of polyesterimide film, it is desirable that the polymerization degree of the polyesterimide precursor be made as high as possible. By achieving polymerization at a monomer concentration in the aforementioned ranges, the polymer polymerization degree becomes sufficiently high and sufficient solubility can also be ensured for the monomer and polymer. If polymerization is achieved at a concentration lower than the aforementioned ranges, the polymerization degree of the polyesterimide precursor may not become sufficiently high. If polymerization is achieved at a monomer concentration higher than the aforementioned ranges, on the other hand, the monomer, and also produced polymer, may not dissolve sufficiently. If an aliphatic diamine is used, salt is sometimes formed in the initial stage of polymerization to interfere with the polymerization. To raise the polymerization degree as much as possible while suppressing the formation of salt, it is desirable that the monomer concentration be managed within the aforementioned favorable ranges at the time of polymerization.

Accordingly, the intrinsic viscosity of the polyesterimide precursor is preferably in a range of 0.1 to 10.0 dL/g, or more preferably in a range of 0.5 to 5.0 dL/g, from the viewpoints of toughness of polyesterimide film and handling of varnish.

The diamine used in the polymerization of a polyesterimide precursor conforming to the present invention is not specifically limited and any diamine can be used as long as it does not reduce the required characteristics of the polyesterimide film or polymerization reactivity of the polyesterimide precursor, which the present invention is intended to achieve. Specific examples include aromatic diamines such as p-phenylenediamine, m-phenylenediamine, 2,4-diaminotoluene, 2,5-diaminotoluene, 2,4-diaminoxylene, 2,4-diaminodurene, 4,4'-diaminodiphenylmethane, 4,4'-methylene bis(2-methylaniline), 4,4'-methylene bis(2-ethylaniline), 4,4'-methylene bis(2,6-dimethylaniline), 4,4'-methylene bis(2,6-diethylaniline), 4,4'-diaminodiphenyl ether, 3,4'-diaminodiphenyl ether, 3,3'-diaminodiphenyl ether, 2,4'-diaminodiphenyl ether, 4,4'-diaminodiphenylsulfone, 3,3'-diaminodiphenylsulfone, 4,4'-diaminobenzophenone, 3,3'-diaminobenzophenone, 4,4'-diaminobenzanilide, 4-aminophenyl-4'-aminobenzoate, benzidine, 3,3'-dihydroxybenzidine, 3,3'-dimethoxybenzidine, o-tridine, m-tridine, 2,2'-bis(trifluoromethyl)benzidine, 1,4-bis(4-aminophenoxy)benzene, 1,3-bis(4-aminophenoxy)benzene, 1,3-bis(3-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-aminophenyl)hexafluoropropane, and p-terphenylenediamine, among others.

In addition, aliphatic diamines include chain aliphatic or alicyclic diamines, where examples of alicyclic diamines include 4,4-methylene bis(cyclohexylamine), isophoronediamine, trans-1,4-diaminocyclohexane, cis-1,4-diaminocyclohexane, 1,4-cyclohexane bis(methyl amine), 2,5-bis(aminomethyl)bicyclo [2.2.1]heptane, 2,6-bis(aminomethyl)bicyclo[2.2.1]heptane, 3,8-bis(aminomethyl)tricyclo [5.2.1.0]decane, 1,3-diaminoadamantane, 2,2-bis(4-aminocyclohexyl)propane, and 2,2-bis(4-aminocyclohexyl)hexafluoropropane, among others, while examples of chain aliphatic diamines include 1,3-propanediamine, 1,4-tetramethylenediamine, 1,5-pentamethylenediamine, 1,6-hexamethylenediamine, 1,7-heptamethylenediamine, 1,8-octamethylenediamine, and 1,9-nonamethylenediamine, among others. In addition, two or more of these diamines can be combined.

As for the diamine, it is preferable to use, as the diamine component, a diamine having a rigid and straight structure such as p-phenylene diamine, 2,5-diaminotoluene, 3,4'-diaminodiphenyl ether, 4,4'-diaminobenzanilide, 4-aminophenyl-4'-aminobenzoate, benzidine, 3,3'-dihydroxybenzidine, 3,3'-dimethoxybenzidine, o-tridine, m-tridine, 2,2'-bis(trifluoromethyl)benzidine, p-terphenylenediamine, or trans-1,4-diaminocyclohexane, among others, from the viewpoint of expressing low heat expansion characteristics of the polyesterimide film. At this time, the content of the aforementioned diamine is 5 to 100 percent by mol, or preferably 30 to 95 percent by mol, relative to the total amount of diamine used.

In the polymerization of a polyesterimide precursor conforming to the present invention, any aromatic or aliphatic tetracarboxylic acid dianhydride, other than tetracarboxylic acid dianhydrides containing ester group which conform to the present invention and are expressed by general formula (1), can be used together, as a copolymerization component, to the extent that it does not significantly reduce the polymerization reactivity of the polyesterimide precursor or required characteristics of the polyesterimide. The aromatic tetracarboxylic acid dianhydride that can be used here is not specifically limited, but examples include pyromellitic acid dianhydride, 3,3',4,4'-biphenyltetracarboxylic acid dianhydride, hydroquinone-bis(trimellitate anhydride), methylhydroquinone-bis(trimellitate anhydride), 1,4,5,8-naphthalene tetracarboxylic acid dianhydride, 2,3,6,7-naphthalene tetracarboxylic acid dianhydride, 3,3',4,4'-benzophenone tetracarboxylic acid dianhydride, 3,3',4,4'-biphenyl ether tetracarboxylic acid dianhydride, 3,3',4,4'-biphenylsulfone tetracarboxylic acid dianhydride, 2,2'-bis(3,4-dicarboxyphenyl)hexafluoropropanic acid dianhydride, and 2,2'-bis(3,4-dicarboxyphenyl)propanic acid dianhydride, among others.

The aliphatic tetracarboxylic acid dianhydride is not specifically limited, but examples include alicyclic types such as bicyclo[2.2.2]octo-7-en-2,3,5,6-tetracarboxylic acid dianhydride, 5-(dioxotetrahydrofuryl-3-methyl-3-cyclohexene-1,2-dicarboxylic acid anhydride, 4-(2,5-dioxotetrahydrofurane-3-yl)tetralin-1,2-dicarboxylic acid anhydride, tetrahydrofurane-2,3,4,5-tetracarboxylic acid dianhydride, bicyclo-3,3',4,4'-tetracarboxylic acid dianhydride, 1,2,3,4-cyclobutane tetracarboxylic acid dianhydride, and 1,2,3,4-cyclopentane tetracarboxylic acid dianhydride, among others. Also, two or more of the foregoing can be combined.

The content of the aforementioned aromatic or aliphatic tetracarboxylic acid dianhydride, which is combined with the ester group-containing tetracarboxylic acid dianhydride which conforms to the present invention and is expressed by general formula (1), is 0 to 95 percent by mol, or preferably 1 to 50 percent by mol, relative to the total amount of tetracarboxylic acid dianhydride used.

As for the solvent used at the time of polymerization reaction, aprotic solvents are preferable such as N,N-dimethylformamide, N,N-dimethylacetoamide, N-methyl-2-pyrrolidone, and dimethylsulfoxide, among others. However, the structure of such solvent is not specifically limited because no problem is anticipated as long as the material monomer and resulting polyesterimide precursor can be dissolved in the solvent. Specific examples of these solvents that can be used favorably include the following, among others: N,N-dimethylformamide, N,N-dimethylacetoamide, N-methylpyrrolidone and other amide solvents; γ-butyrolactone, γ-valerolactone, δ-valerolactone, γ-caprolactone, ∈-caprolactone, α-methyl-γ-butyrolactone and other cyclic ester solvents; ethylene carbonate, propylene carbonate and other carbonate solvents; triethylene glycol and other glycol solvents; m-cresol, p-cresol, 3-chlorophenol, 4-chlorophenol and other phenol solvents; acetophenone, 1,3-dimethyl-2-imidazolidinone, sulfolane, and dimethyl sulfoxide. Furthermore, other general organic solvents can also be added, such as phenol, o-cresol, butylacetate, ethylacetate, isobutylacetate, propyleneglycolmethyl acetate, ethylcellosolve, butylcellosolve, 2-methylcellosolve acetate, ethylcellosolveacetate, butylcellosolveacetate, tetrahydrofuran, dimethoxyethane, diethoxyethane, dibutylether, diethyleneglycoldimethyl ether, methylisobutylketone, diisobutyl ketone, cyclohexanone, methylethyl ketone, acetone, butanol, ethanol, xylene, toluene, chlorobenzene, terpene, mineral spirits, and petroleum naphtha solvents.

The polyesterimide precursor conforming to the present invention can be isolated as powder by dripping its polymerization solution into an ample amount of water, methanol or other poor solvent, filtering and drying.

A novel polyesterimide derived from a polyesterimide precursor, which is yet another aspect of the present invention, can be produced by cyclodehydrating (imidizing) a polyesterimide precursor, which was obtained by the aforementioned method, using any known method as deemed appropriate. At this time, the form of polyesterimide is not specifically limited, but examples include film, metal foil/polyesterimide film laminate, powder, molding, and varnish, among others.

First, how to produce a polyesterimide film conforming to the present invention is explained using an example. Polymerization solution (varnish) of a polyesterimide precursor conforming to the present invention is poured onto a substrate made of glass, copper, aluminum, stainless steel, silicon, etc., and the substrate is dried in an oven at 40 to 180° C., or preferably at 50 to 150° C. Next, the obtained polyesterimide precursor film is heated on the substrate in vacuum, in nitrogen or other inert gas, or in air at 200 to 450° C., or preferably at 250 to 400° C., to produce a polyesterimide film conforming to the present invention. The heating temperature is preferably 200° C. or above from the viewpoint of achieving sufficient cyclization reaction for imidization, and preferably 450° C. or below from the viewpoint of making the produced polyesterimide film thermally stable. Also, while imidization is desirably achieved in vacuum or inert gas, it can also be achieved in air as long as the imidization temperature does not become too high.

Instead of using heat treatment, imidization reaction can also be achieved by soaking a polyesterimide precursor film in a solution containing acetic acid anhydride or other cyclodehydration reagent in the presence of pyridine, triethyl amine or other tertiary amine. In addition, it is possible to introduce such cyclodehydration reagent into a polyesterimide precursor varnish and agitate the mixture, and then pour the agitated mixture onto the aforementioned substrate and dry the substrate, in order to produce a partially imidized polyesterimide precursor film. When this film is heat-treated as explained above, a polyesterimide film can be obtained.

Varnish of a polyesterimide conforming to the present invention can be produced with ease if the polyimide itself dissolves in the solvent used, when the polymerization solution of a polyesterimide precursor conforming to the present invention is heated to a range of 150 to 250° C., either directly or after diluting with the same solvent as deemed appropriate. If the polyimide does not dissolve in the solvent, crystalline polyesterimide powder can be obtained as precipitate. At this time, toluene, xylene, etc., can be added to remove water and other byproducts of imidization by means of azeotropic distillation. Also, γ-picoline or other base can be added as a catalyst. When the obtained varnish is dripped into an ample amount of water, methanol or other poor solvent and the mixture is filtered, polyesterimide can be isolated in powder form. In addition, this polyesterimide powder can be dissolved again in the aforementioned polymerization solvent to obtain polyimide varnish.

A polyesterimide conforming to the present invention can be polymerized in a single step by causing a tetracarboxylic acid dianhydride conforming to the present invention to react with a diamine at high temperature in a solvent, without having to isolate the polyesterimide precursor. At this time, the reaction solution is retained at temperatures normally in a range of 130 to 250° C., or preferably in a range of 150 to 200° C., from the viewpoint of promoting the reaction. If the polyesterimide does not dissolve in the solvent used, then the polyesterimide can be obtained as precipitate. If it dissolves in the solvent, polyesterimide varnish is obtained. Although the polymerization solvent is not specifically limited, examples of solvents that can be used include N,N-dimethylformamide, N,N-dimethylacetoamide, N-methyl-2-pyrrolidone, dimethyl sulfoxide and other aprotic solvents, where m-cresol and other phenol solvents or NMP and other amide solvents are more preferable. Toluene, xylene, etc., can be added to these solvents in order to remove water, which is a byproduct of imidization, by means of azeotropic distillation. Also, γ-picoline or other base can be added as an imidization catalyst. When the obtained varnish is dripped into an ample amount of water, methanol or other poor solvent and the mixture is filtered, polyesterimide can be isolated in powder form. If this polyesterimide powder can be dissolved in the aforementioned solvent, it is possible to dissolve the powder in the solvent again to obtain polyesterimide varnish.

A polyesterimide film can also be formed by coating onto a substrate the aforementioned polyesterimide varnish thus obtained and drying the substrate at temperatures normally in a range of 40 to 400° C., or preferably in a range of 100 to 350° C.

A molding of polyesterimide can be produced by heating and compressing the polyesterimide powder as obtained above, at temperatures normally in a range of 200 to 500° C., or preferably in a range of 250 to 450° C.

Furthermore, polyester isoimide, which is an isomer of polyesterimide, can be produced when N,N-dicyclohexyl carbodiimide, trifluoro acetic acid anhydride or other dehydration reagent is added to a polyesterimide precursor solution conforming to the present invention, and then the mixture is agitated to cause reaction at temperatures normally in a range of 0 to 150° C., or preferably in a range of 20 to 100° C. Isoimidization reaction can also be achieved by soaking a polyesterimide precursor film in a solution containing the aforementioned dehydration reagent. By producing a film of polyester isoimide varnish using the same procedure explained above, and then heat-treating the varnish at temperatures normally in a range of 250 to 450° C. or preferably in a range of 270 to 400° C., the polyester isoimide varnish can be easily converted to polyesterimide.

EXAMPLES

The present invention is explained in greater detail below using examples, but it should be noted that the present invention is not at all limited to these examples. In the above, the physical property values referenced in the following examples were measured by the methods specified below.
<Infrared Absorption Spectrum>
Infrared absorption spectra of tetracarboxylic acid dianhydrides containing ester group were measured by the KBr method using a Fourier transform infrared spectrophotometer (FT-IR5300 or FT-IR350 by JASCO Corporation). Also, infrared absorption spectra of thin films (thickness: approx. 5 µm) of polyesterimide precursors and polyesterimides were measured by the transmission method.
<$^1$H-NMR Spectrum>
$^1$H-NMR spectra of tetracarboxylic acid dianhydrides containing ester group were measured in a deuterated dimethyl sulfoxide using a NMR spectrophotometer (ECP400) by JEOL Ltd.
<Differential Scanning Calorimetry (Melting Point and Melt Curve)>
Melting points and melt curves (DSC curves) of tetracarboxylic acid dianhydrides containing ester group were measured in an atmosphere of nitrogen by raising the temperature at a rate of 2° C. per minute using a differential scanning calorimeter (DSC3100) by Bruker AXS. The higher the melting point and sharper the melting peak, the higher the purity.
<Intrinsic Viscosity>
0.5% (by weight) polyesterimide precursor solutions were measured at 30° C. using an Ostwald viscometer.
<Glass Transition Temperature: Tg>
Glass transition temperatures of polyesterimide films (thickness: 20 µm) were obtained from the loss peaks at a frequency of 0.1 Hz by raising the temperature at a rate of 5° C. per minute by means of dynamic viscoelasticity measurement using a thermo-mechanical analyzer (TMA4000) by Bruker AXS.
<Linear Heat Expansion Coefficient: CTE>
Linear heat expansion coefficients of polyesterimide films (thickness: 20 µm) were obtained as an average over a range of 100 to 200° C. from the elongations of test pieces at a load of 0.5 g per 1 µm of film thickness by raising the temperature at a rate of 5° C. per minute by means of thermo-mechanical analysis using a thermo-mechanical analyzer (TMA4000) by Bruker AXS.
<5% Weight Loss Temperature: $T_d^5$>
Temperatures at which the initial weights of polyesterimide films (thickness: 20 µm) decreased by 5% were measured during the course of temperature rise at a rate of 10° C. per minute, in nitrogen or air, using a thermal weight analyzer (TG-DTA2000) by Bruker AXS. The higher the measured temperature, the higher the thermal stability.
<Birefringence: Δ>
Refractive indexes of polyesterimide films (thickness: 20 µm) were measured in the direction parallel to the film ($n_{in}$) and also in the direction vertical to the film ($n_{out}$), using an Abbe refractometer (Abbe 4T) by Atago Co., Ltd. (using a sodium lamp at a wavelength of 589 nm), and birefringences were obtained from the difference between the two refractive indexes ($\Delta = n_{in} - n_{out}$). The higher this value, the higher the degree of in-plane orientation of the polymer chain.
<Dielectric Constant: $\epsilon_{cal}$>
Dielectric constants ($\epsilon_{cal}$) of polyesterimide films were calculated by the formula $\epsilon_{cal} = 1.1 \times n_{av}^2$ based on the average refractive index [$n_{av} = (2n_{in} + n_{out})/3$] of polyesterimide films using an Abbe refractometer (Abbe 4T) by Atago Co., Ltd.
<Water Absorption Coefficient>
Polyesterimide films (thickness: 20 to 30 µm) that had been vacuum-dried for 24 hours at 50° C. were soaked for 24 hours in 24° C. water, after which excess water was wiped off and the water absorption coefficient (%) of each film was obtained from the increase in weight. In most applications, it is desirable for this value to be as low as possible.
<Modulus of Elongation (Young's Modulus), Breaking Strength, Breaking Elongation>
Test pieces (3 mm×30 mm) of polyesterimide films (thickness: 20 µm) were subjected to a tensile test (rate of elongation: 8 mm/min) using a tensile tester (Tensilon UTM-II) by Toyo Baldwin Co., Ltd. to obtain the modulus of elasticity of each film from the initial slope of the stress vs. strain curve, as well as breaking elongation (%) from the rate of elongation at which the film broke. The higher the breaking elongation, the higher the toughness of film. The breaking strength was obtained from the stress at which the test piece broke.

<Coefficient of Hygroscopic Expansion: CHE>

Polyesterimide films (5 mm×20 mm×thickness 20 μm) were vacuum-dried for several hours at 100° C., and then immediately set on a thermo-mechanical analyzer (TMA4000) by Bruker AXS (chuck interval: 15 mm), after which a static load of 0.5 g per 1 μm of film thickness was applied to the test pieces. Then, dry nitrogen was supplied for 1 hour at room temperature, after which wet gas of 80% in relative humidity (RH) was introduced into the TMA4000 system using a precision humidifier (SRG-1R-1) by Shinyei Kaisha to obtain the coefficient of hygroscopic expansion of each polyesterimide film from the elongation of the test piece at room temperature. The lower this value, the higher the hygroscopic dimensional stability.

Example 1

Synthesis of Ester Group-containing tetracarboxylic acid dianhydride

An ester group-containing tetracarboxylic acid dianhydride as expressed by formula (21) was synthesized as follows. 30 mmol of trimellitic acid chloride was put in an eggplant flask, after which anhydrous tetrahydrofuran was introduced to dissolve trimellitic acid chloride and septum seal was applied to prepare solution A (solute concentration: 20 percent by weight). In another flask, DHTP-M (15 mmol) was dissolved in anhydrous tetrahydrofuran and then 60 mmol of pyridine was added, after which septum seal was applied to prepare solution B (solute concentration: 20 percent by weight).

Figure 2:
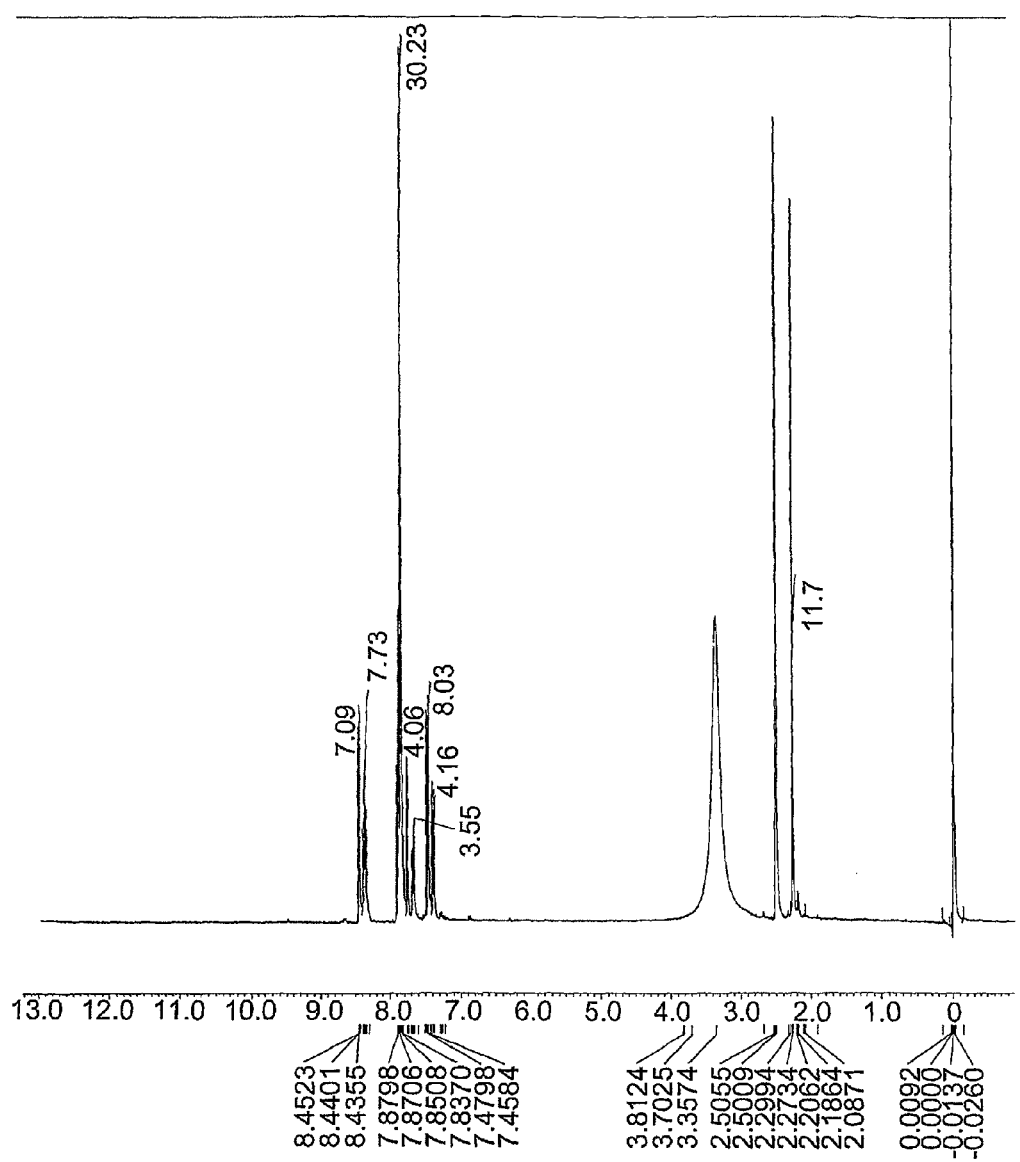
[FIG. 2] $^1$H-NMR spectrum of the ester group-containing tetracarboxylic acid dianhydride described in Example 1.
Figure 3:
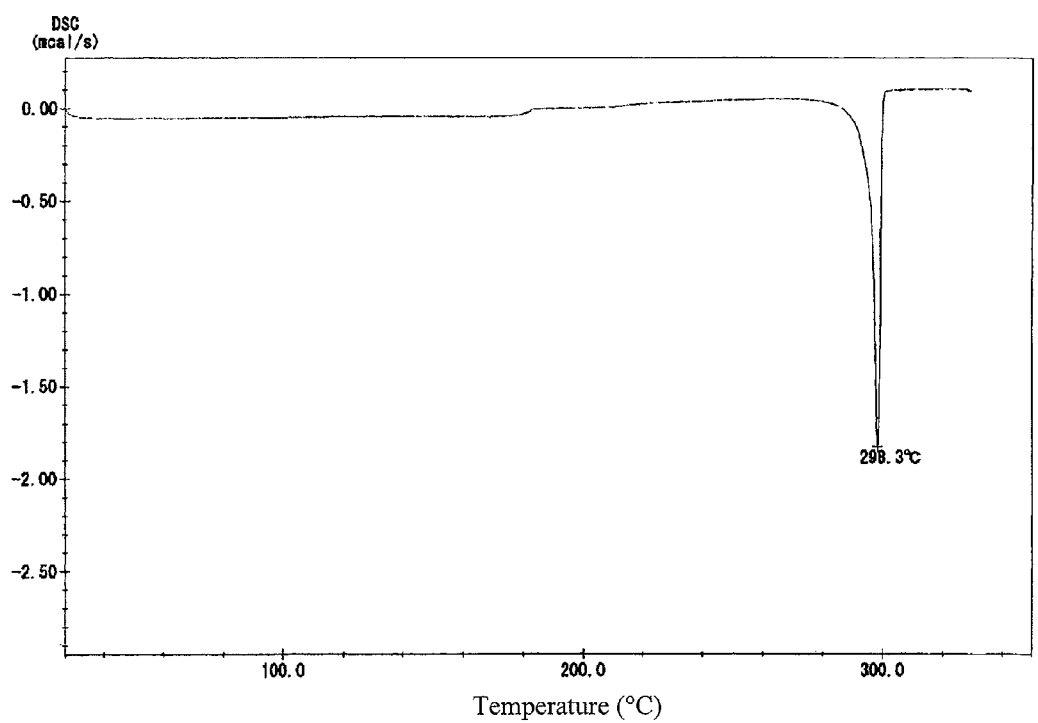
[FIG. 3] Differential scanning calorimetric curve of the ester group-containing tetracarboxylic acid dianhydride described in Example 1.

Solution B was dripped into solution A over a period of 1 hour using a syringe while cooling and agitating the mixture in an ice bath, after which tetrahydrofuran was added to dilute the mixture until the solute concentration became 12 percent by weight, and then the diluted mixture was agitated for 24 hours at room temperature. After the reaction had completed, white precipitate (mixture of the target substance and pyridine hydrochloride) was filtered out and the precipitate was washed with an ample amount of water to dissolve and eliminate pyridine hydrochloride, after which the obtained light yellow precipitate was vacuum-dried for 24 hours at 150° C. to obtain a product at a yield of 70%. From the infrared absorption spectrum and $^1$H-NMR spectrum, the obtained product was confirmed to be the target ester group-containing tetracarboxylic acid dianhydride as expressed by formula (21). Also, the differential scanning calorimetric curve showed a sharp melting peak at 297° C., which suggests that this product had high purity. The infrared absorption spectrum, $^1$H-NMR spectrum and differential scanning calorimetric curve are shown in FIGS. 1, 2 and 3, respectively.

Example 2

Synthesis of Ester Group-containing tetracarboxylic acid dianhydride

An ester group-containing tetracarboxylic acid dianhydride as expressed by formula (16) was synthesized as follows. 60 mmol of trimellitic acid chloride was put in an eggplant flask, after which 40 mL of anhydrous N,N-dimethyl formamide (DMF) was introduced to dissolve trimellitic acid chloride at room temperature and then septum seal was applied to prepare solution A (solute concentration: 25 percent by weight). In another flask, 20 mmol of a diol expressed by formula (6) (referred to as "OC-BP") was dissolved in 14 mL of anhydrous DMF at room temperature (solute concentration: 25 percent by weight), and then 180 mmol of pyridine was added, after which septum seal was applied to prepare solution B.

Figure 4:
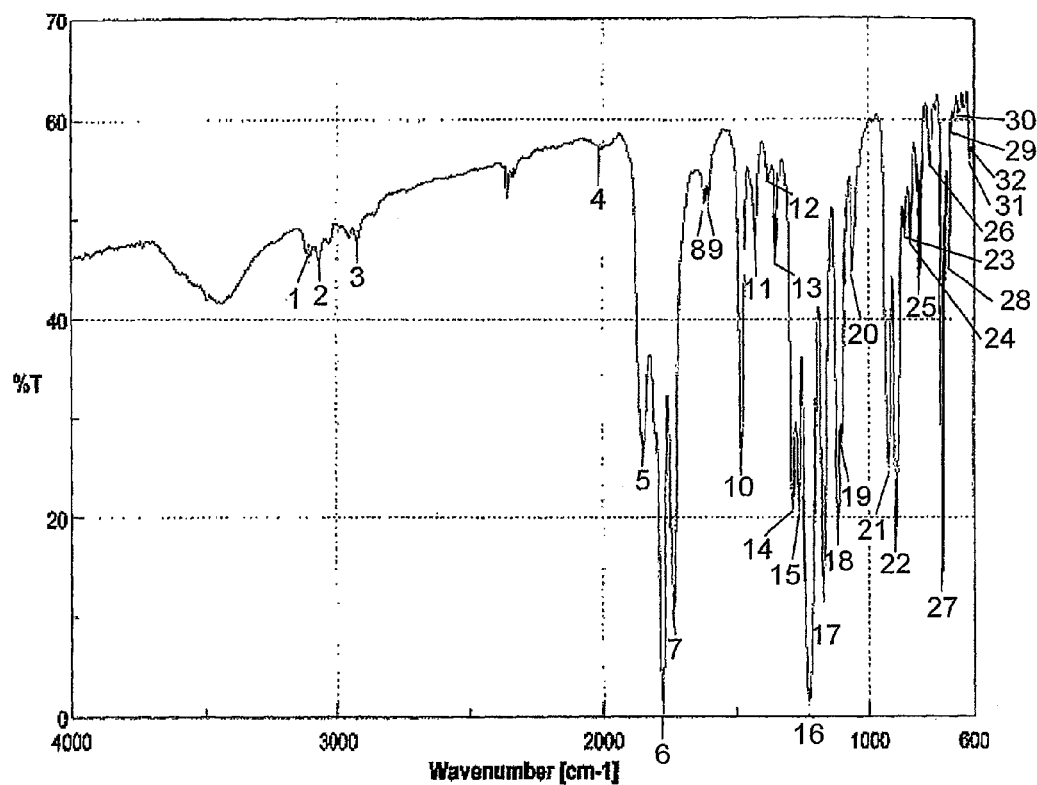
[FIG. 4] Infrared absorption spectrum of the ester group-containing tetracarboxylic acid dianhydride described in Example 2.
Figure 5:
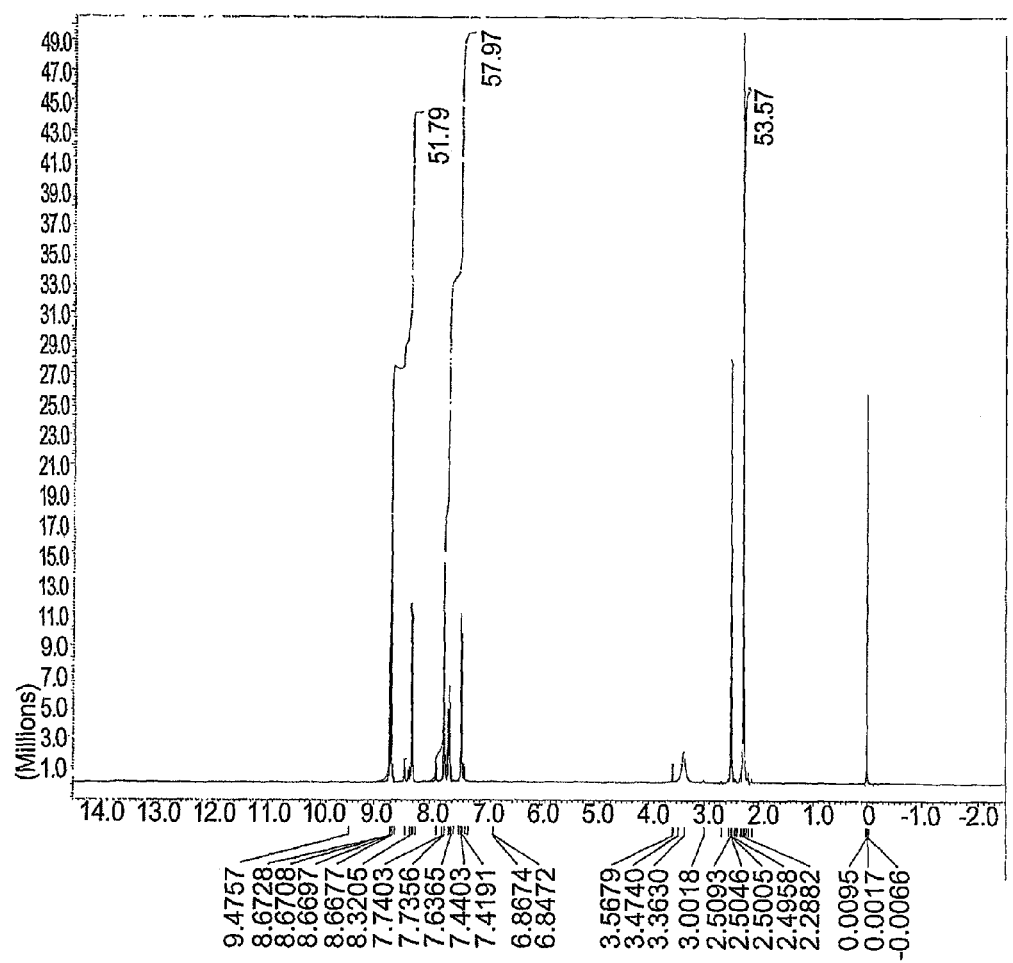
[FIG. 5] $^1$H-NMR spectrum of the ester group-containing tetracarboxylic acid dianhydride described in Example 2.
Figure 6:
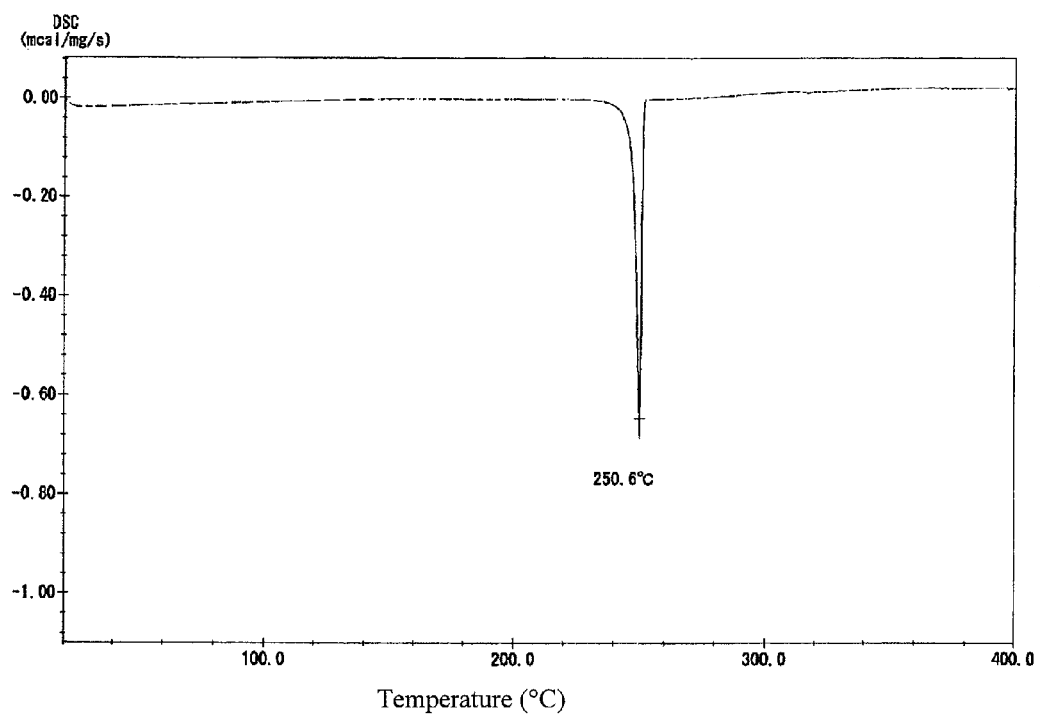
[FIG. 6] Differential scanning calorimetric curve of the ester group-containing tetracarboxylic acid dianhydride described in Example 2.

Solution B was dripped into solution A using a syringe while cooling and agitating the mixture in an ice bath, after which the mixture was agitated for 12 hours at room temperature. After the reaction had completed, yellow precipitate (mixture of the target substance and pyridine hydrochloride) was filtered out and the precipitate was washed with an ample amount of water to dissolve and eliminate pyridine hydrochloride, after which the obtained yellow precipitate was vacuum-dried for 12 hours at 160° C. to obtain a crude product at a yield of 80%. To increase the purity further, the crude product was recrystallized using anhydrous 1,4-dioxane, after which the educed precipitate was filtered out and vacuum-dried for 12 hours at 160° C. to obtain a product. From the infrared absorption spectrum and $^1$H-NMR spectrum, the obtained product was confirmed to be the target ester group-containing tetracarboxylic acid dianhydride as expressed by formula (16). Also, the differential scanning calorimetric curve showed a sharp melting peak at 251° C., which suggests that this product had high purity. The infrared absorption spectrum, $^1$H-NMR spectrum and differential scanning calorimetric curve are shown in FIGS. 4, 5 and 6, respectively.

Example 3

Synthesis of Ester Group-containing tetracarboxylic acid dianhydride

An ester group-containing tetracarboxylic acid dianhydride as expressed by formula (18) was synthesized as follows. 20 mmol of trimellitic acid chloride was put in an eggplant flask, after which anhydrous THF was introduced to dissolve trimellitic acid chloride at room temperature and then septum seal was applied to prepare solution A (solute concentration: 15 percent by weight). In another flask, 10 mmol of a diol expressed by formula (8) (referred to as "TMP-BP") was dissolved in anhydrous THF at room temperature (solute concentration: 15 percent by weight), and then 30 mmol of pyridine was added, after which septum seal was applied to prepare solution B.

Figure 7:
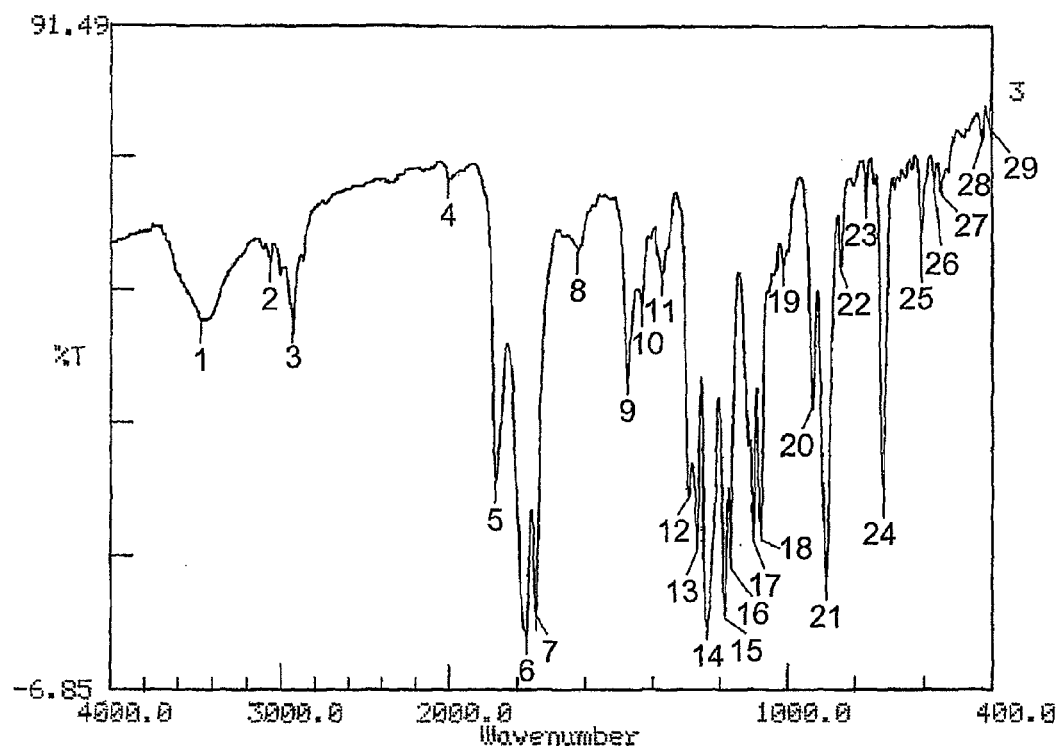
[FIG. 7] Infrared absorption spectrum of the ester group-containing tetracarboxylic acid dianhydride described in Example 3.

Solution B was dripped into solution A using a syringe while cooling and agitating the mixture in an ice bath, after which the mixture was agitated for 12 hours at room temperature. After the reaction had completed, white precipitate (pyridine hydrochloride) was filtered out and then the filtrate was condensed using an evaporator and the condensed filtrate was dripped into an ample amount of water. The educed precipitate was washed thoroughly with water to dissolve and eliminate pyridine hydrochloride, after which the obtained yellow precipitate was vacuum-dried for 12 hours at 80° C. to obtain a crude product. To increase the purity further, the crude product was recrystallized using acetic acid anhydride, after which the educed precipitate was filtered out, washed with toluene, and then vacuum-dried for 12 hours at 80° C. to obtain a product. From the infrared absorption spectrum, the obtained product was confirmed to be the target ester group-containing tetracarboxylic acid dianhydride as expressed by formula (18). The infrared absorption spectrum is shown in FIG. 7.

Example 4

Synthesis of Ester Group-containing tetracarboxylic acid dianhydride

An ester group-containing tetracarboxylic acid dianhydride as expressed by formula (20) was synthesized as follows. 15 mmol of trimellitic acid chloride was put in an eggplant flask, after which 30 mL of anhydrous DMF was introduced to dissolve trimellitic acid chloride at room temperature and then septum seal was applied to prepare solution A (solute concentration: 10 percent by weight). In another flask, 5 mmol of a diol expressed by formula (10) (referred to as "DHTP") was dissolved in 13 mL of anhydrous DMF by heating to 50° C. (solute concentration: 10 percent by weight), and then 30 mmol of pyridine was added, after which septum seal was applied to prepare solution B.

Figure 8:
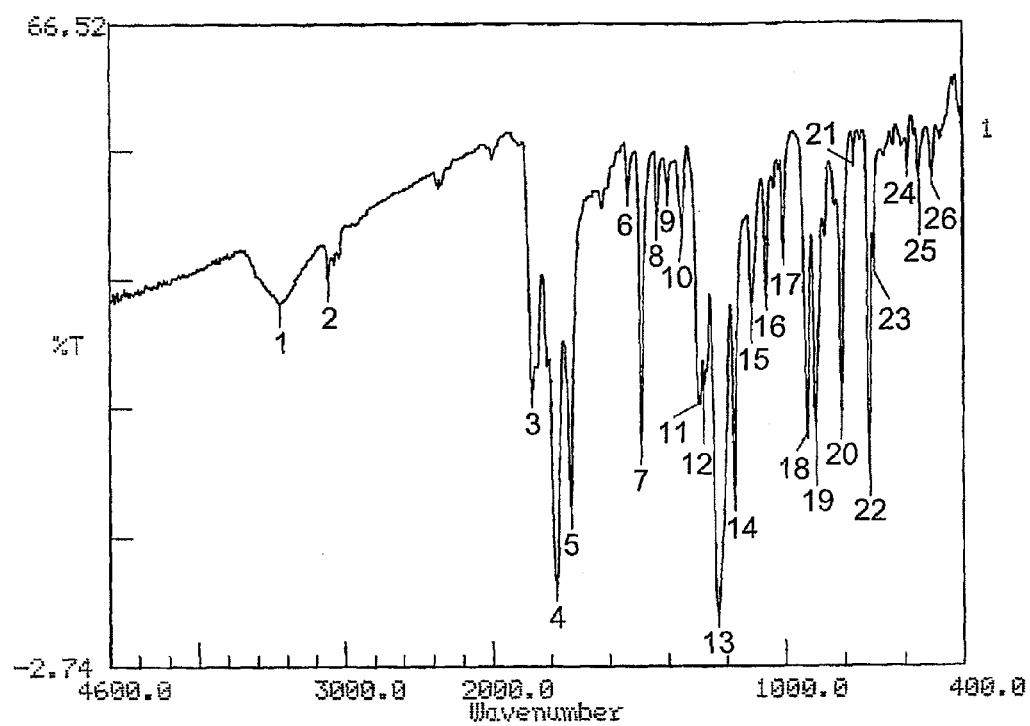
[FIG. 8] Infrared absorption spectrum of the ester group-containing tetracarboxylic acid dianhydride described in Example 4.
Figure 9:
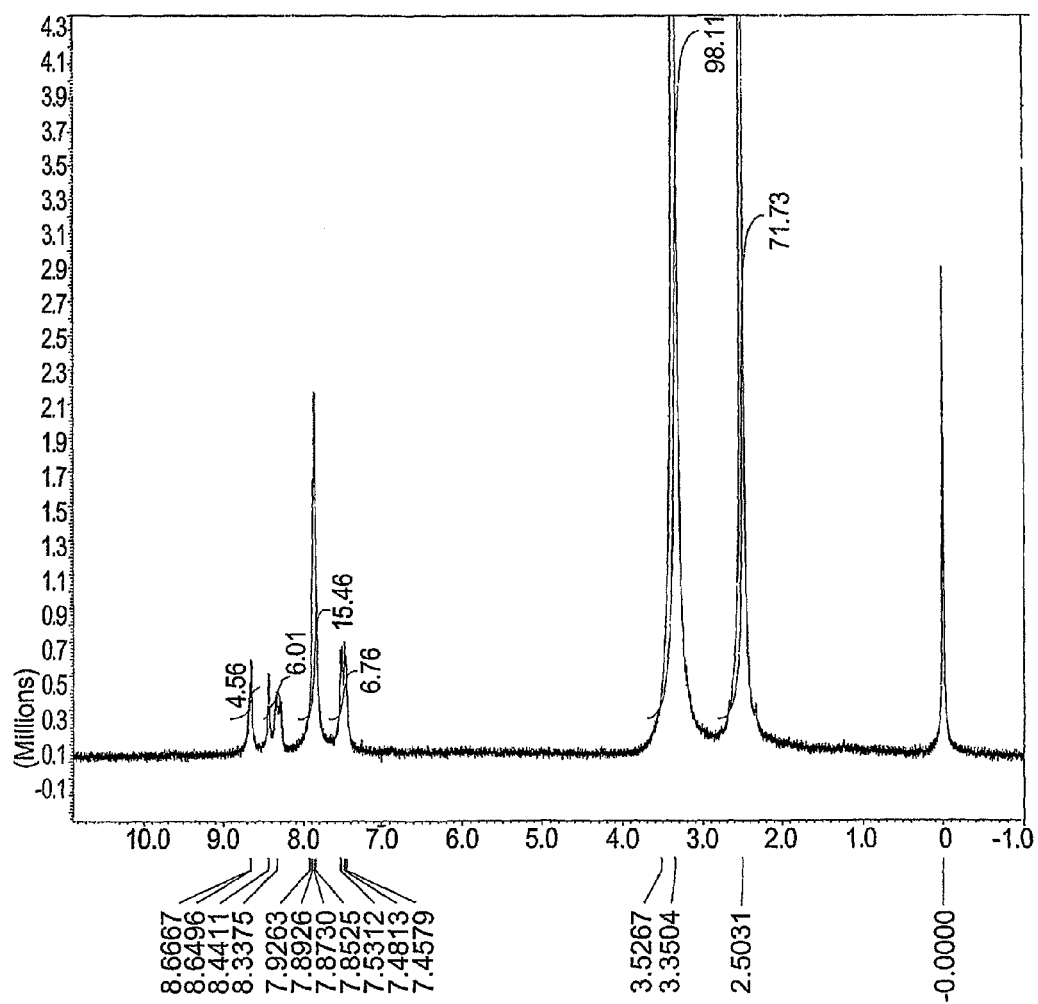
[FIG. 9] $^1$H-NMR spectrum of the ester group-containing tetracarboxylic acid dianhydride described in Example 4.

Solution B was dripped into solution A using a syringe while agitating the mixture at room temperature, after which 20 mL of DMF was added to dilute the mixture, which was then agitated for 24 hours at room temperature. After the reaction had completed, yellow precipitate (mixture of the target substance and pyridine hydrochloride) was filtered out and washed with DMF. The precipitate was then washed further with an ample amount of water to dissolve and eliminate pyridine hydrochloride, after which the obtained yellow precipitate was vacuum-dried for 12 hours at 180° C. to obtain a product at a yield of 80%. From the infrared absorption spectrum and $^1$H-NMR spectrum, the obtained product was confirmed to be the target ester group-containing tetracarboxylic acid dianhydride as expressed by formula (20). Also, the differential scanning calorimetric curve showed a sharp melting peak at 337° C., which suggests that this product had high purity. The infrared absorption spectrum and $^1$H-NMR spectrum are shown in FIGS. 8 and 9, respectively.

Example 5

Synthesis of Ester Group-containing tetracarboxylic acid dianhydride

An ester group-containing tetracarboxylic acid dianhydride as expressed by formula (24) was synthesized as follows. 40 mmol of trimellitic acid chloride was put in an eggplant flask, after which 36 mL of anhydrous DMF was introduced to dissolve trimellitic acid chloride at room temperature and then septum seal was applied to prepare solution A (solute concentration: 20 percent by weight). In another flask, 20 mmol of a diol expressed by formula (15) (referred to as "DHQP-TM") was dissolved in 70 mL of anhydrous DMF by heating to 80° C. (solute concentration: 10 percent by weight), and then the mixture was cooled to room temperature and 120 mmol of pyridine was added, after which septum seal was applied to prepare solution B.

Figure 10:
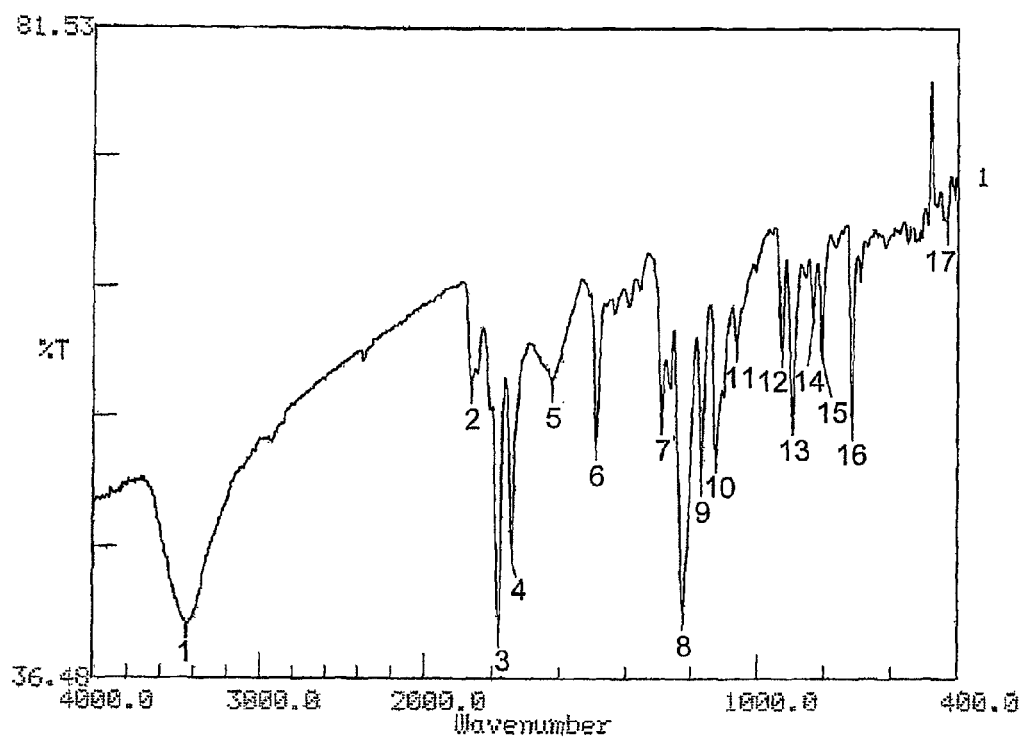
[FIG. 10] Infrared absorption spectrum of the ester group-containing tetracarboxylic acid dianhydride described in Example 5.
Figure 11:
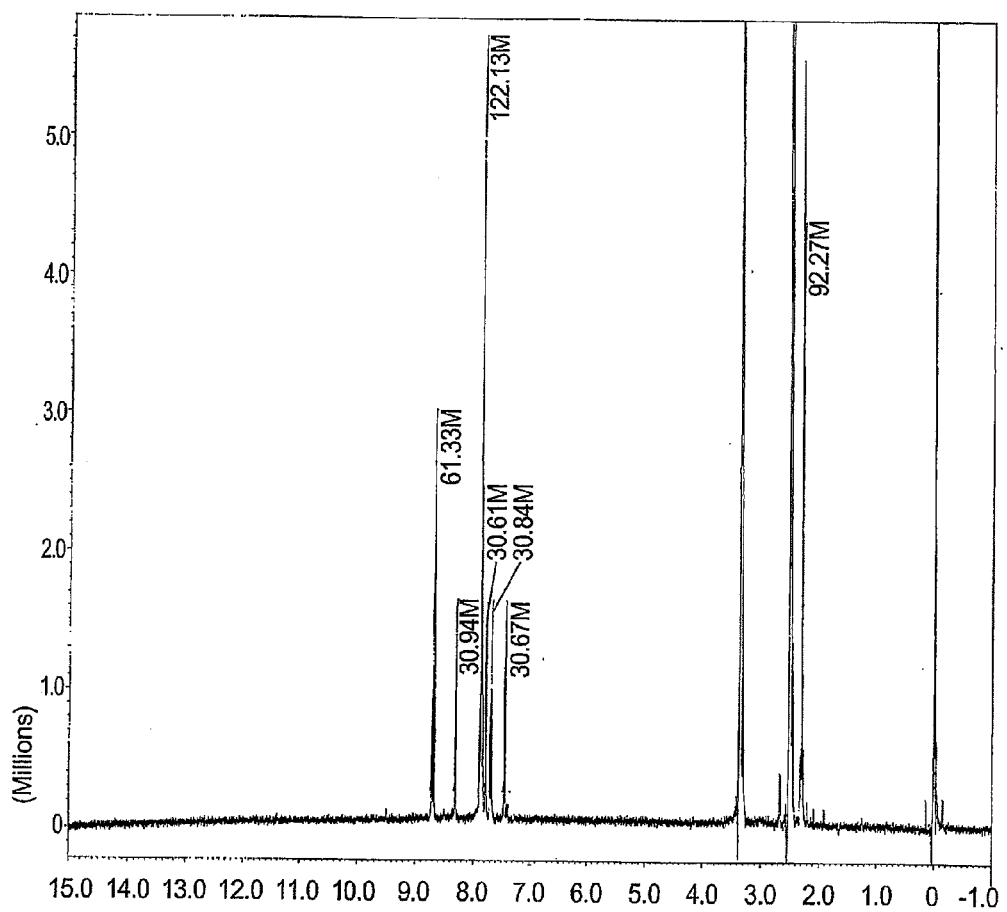
[FIG. 11] $^1$H-NMR spectrum of the ester group-containing tetracarboxylic acid dianhydride described in Example 5.
Figure 12:
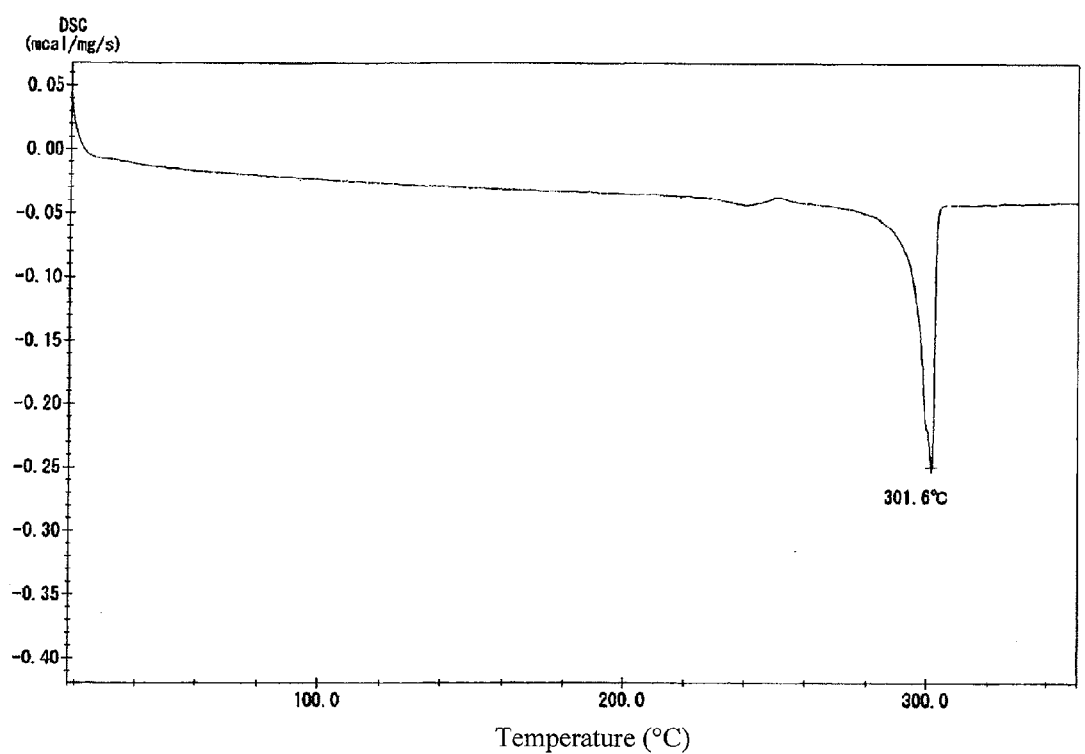
[FIG. 12] Differential scanning calorimetric curve of the ester group-containing tetracarboxylic acid dianhydride described in Example 5.

Solution B was dripped into solution A using a syringe while agitating the mixture at room temperature, after which 20 mL of DMF was added to dilute the mixture, which was then agitated for 24 hours at room temperature. After the reaction had completed, yellow precipitate (mixture of the target substance and pyridine hydrochloride) was filtered out and washed with DMF. The precipitate was then washed further with an ample amount of water to dissolve and eliminate pyridine hydrochloride, after which the obtained yellow precipitate was vacuum-dried for 12 hours at 180° C. to obtain a crude product at a yield of 70%. To increase the purity further, the crude product was recrystallized using γ-butyrolacton, after which the educed precipitate was filtered out, washed with anhydrous THF, and then vacuum-dried for 12 hours at 200° C. to obtain a product. From the infrared absorption spectrum and $^1$H-NMR spectrum, the obtained product was confirmed to be the target ester group-containing tetracarboxylic acid dianhydride as expressed by-formula (24). Also, the differential scanning calorimetric curve showed a sharp melting peak at 302° C., which suggests that this product had high purity. The infrared absorption spectrum, $^1$H-NMR spectrum and differential scanning calorimetric curve are shown in FIGS. 10, 11 and 12, respectively.

Example 6

Polymerization and Imidization of Polyesterimide Precursor, and Evaluation of Polyesterimide Film Characteristics 5 mmol of p-phenylene diamine (hereinafter referred to as "PDA") was put in a thoroughly dried, sealed reaction container with agitator, and then N-methyl-2-pyrrolidone (NMP) that had been thoroughly dehydrated using molecular sieves 4A was introduced to dissolve PDA, after which 5 mmol of the powder of the ester group-containing tetracarboxylic acid dianhydride as expressed by formula (21), which had been obtained in Example 1, was gradually added to the obtained solution (total monomer concentrate: 20 percent by weight). As the viscosity of the solution increased, the same solvent was added gradually to dilute the solution until the total monomer concentration finally became 12 percent by weight. The diluted solution was then agitated for 48 hours to obtain a transparent, viscous and uniform polyesterimide precursor solution. When this polyesterimide precursor solution was left at room temperature and −20° C. for 1 month, precipitation and gelling did not occur at all and the solution exhibited high storage stability. When measured using an Ostwald viscometer in NMP at 30° C. and concentration of 0.5 percent by weight, the intrinsic viscosity of the polyesterimide precursor was 1.72 dL/g, indicating a high polymer. This polyesterimide precursor solution was coated on a glass substrate and the substrate was dried at 60° C. for 2 hours to obtain a polyesterimide precursor film, which was then heated on the substrate at 200° C. for 1 hour under a reduced pressure, and then thermally imidized further at 350° C. for 1 hour, after which the film was separated from the substrate to remove any residual stress, and then heat-treated at 355° C. for 1 hour, to obtain a transparent, light yellow polyesterimide film of 20 μm in thickness. This polyesterimide film did not break, but demonstrated flexibility, in a 180° bending test. Also, the film did not dissolve at all in any organic solvent. When the dynamic viscoelasticity of this polyesterimide film was measured, the glass transition point was observed at 438° C. (determined from the loss peak on the dynamic viscoelasticity curve), but thermoplasticity was virtually non-existent. These results show that this polyesterimide film had extremely high dimensional stability.

Also, the film had a very low linear heat expansion coefficient of 7.3 ppm/K. Judging from the very high birefringence value of the film (Δn=0.17), this extremely low linear heat expansion coefficient is probably due to the high in-plane orientation of the polyesterimide chain. The dielectric constant was estimated to be 3.25 based on the average refractive index, which is lower than the dielectric constant (3.5) of a representative total aromatic polyimide of low heat expansion constituted by 3,3',4,4'-biphenyl tetracarboxylic acid dianhydride and p-phenylene diamine. Also, the glass transition temperature was extremely high at 438° C., while the 5% weight loss temperature was also high, at 479° C. in nitrogen and 451° C. in air. These results indicate that the film had sufficiently high heat resistance. Also, one characteristic of any polyesterimide film conforming to the present invention is that its water absorption coefficient is extremely low, or 0.88% in this example. As for mechanical characteristics, the modulus of elongation (Young's modulus) was 7.66 GPa, breaking strength was 0.16 GPa, and breaking elongation was 3.6%.

Figure 13:
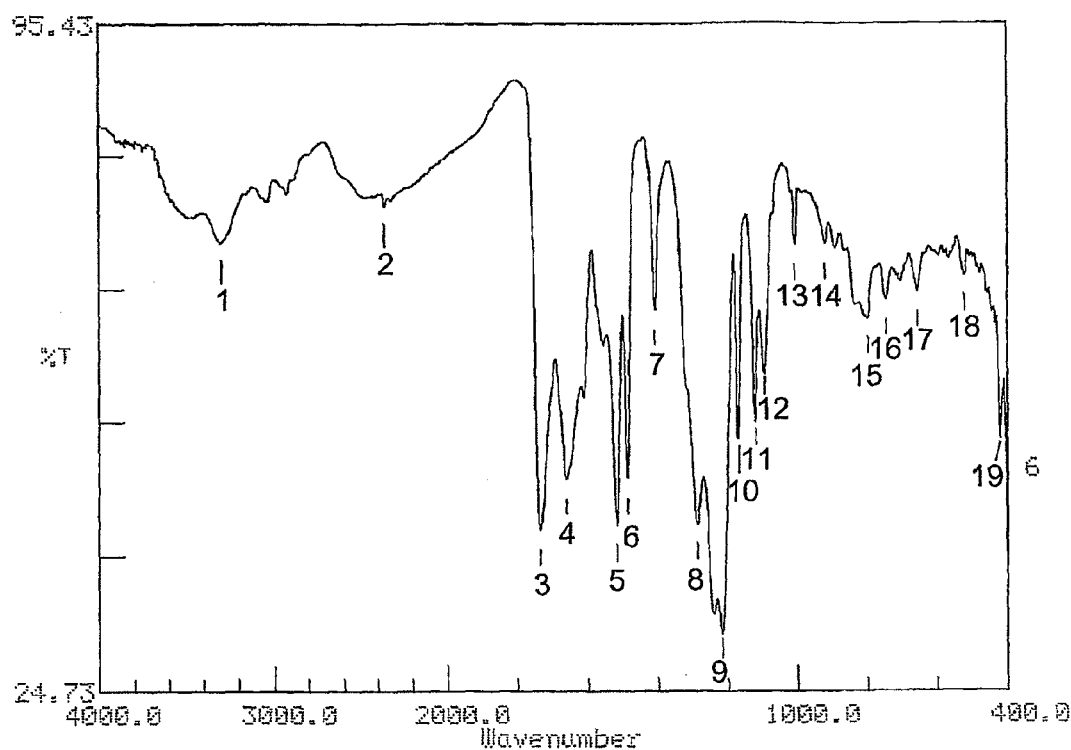
[FIG. 13] Infrared absorption spectrum of a thin film of the polyesterimide precursor described in Example 6.
Figure 14:
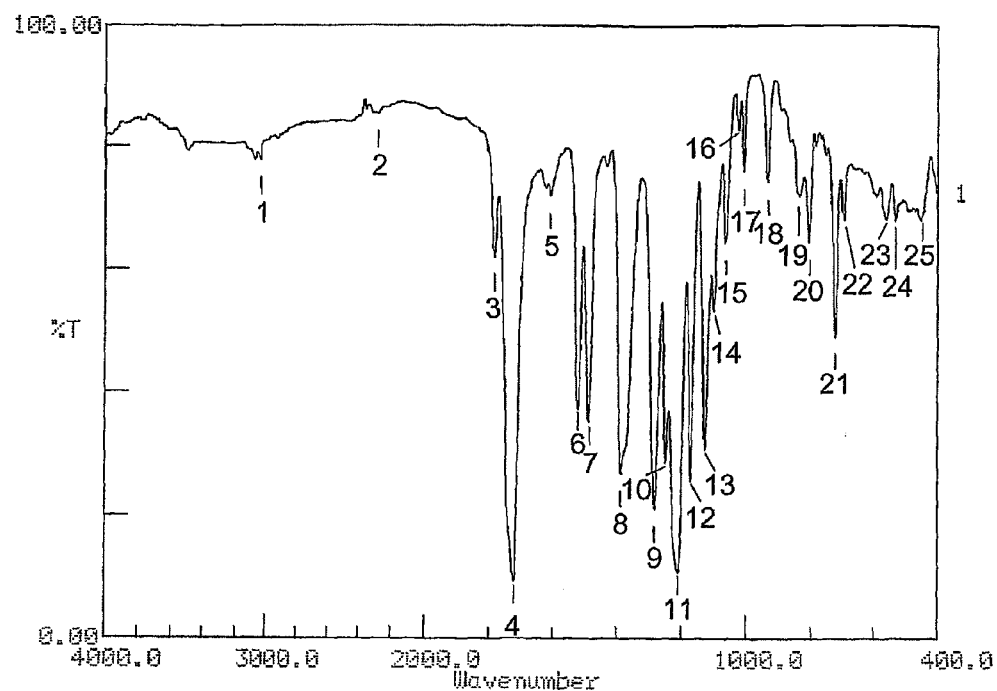
[FIG. 14] Infrared absorption spectrum of a thin film of the polyesterimide described in Example 6.

As described above, this polyesterimide demonstrated extremely low linear heat expansion coefficient, very low water absorption coefficient, high thermal stability, and relatively low dielectric constant. The values of physical properties are summarized in Table 1. The infrared absorption spectra of obtained thin films of polyesterimide precursor and polyesterimide are shown in FIGS. 13 and 14, respectively.

Example 7

Figure 15:
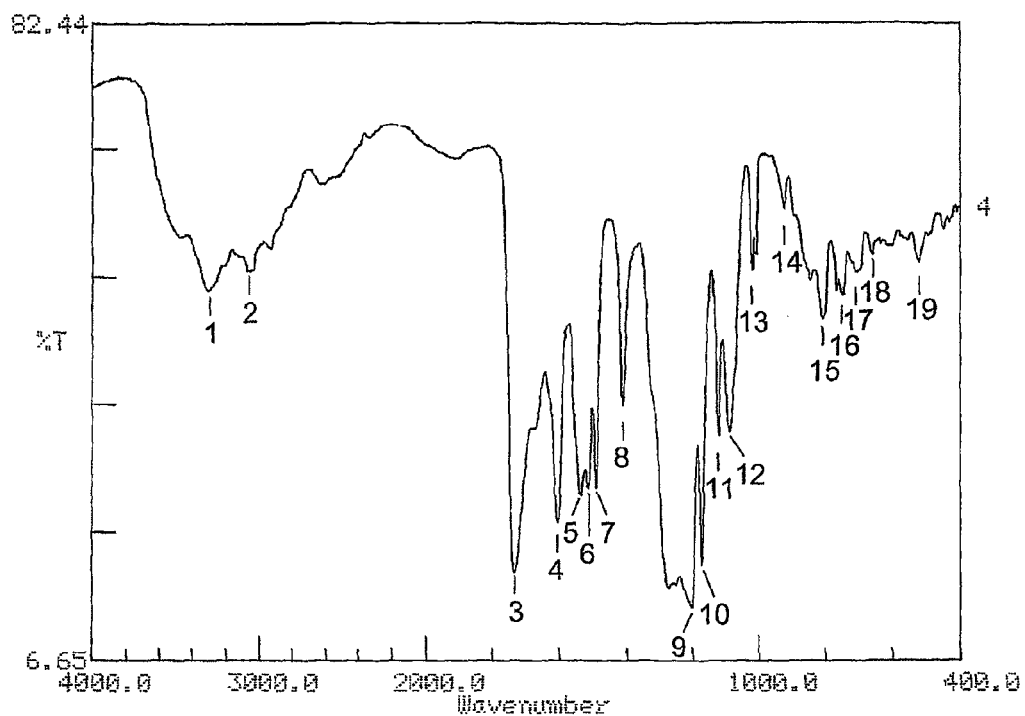
[FIG. 15] Infrared absorption spectrum of a thin film of the polyesterimide precursor described in Example 7.
Figure 16:
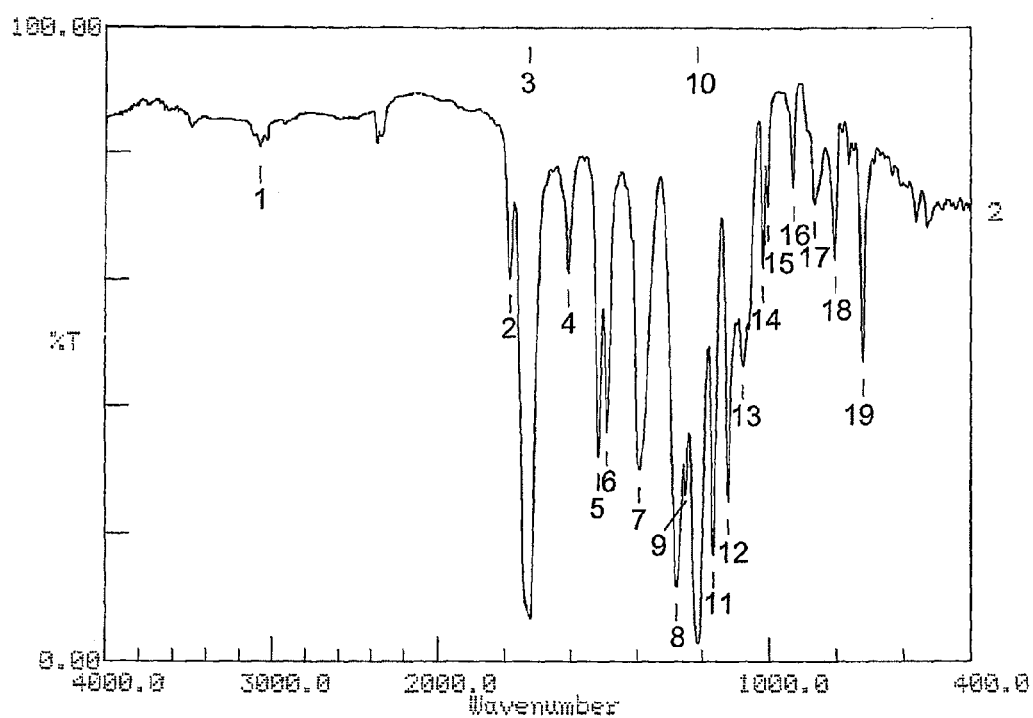
[FIG. 16] Infrared absorption spectrum of a thin film of the polyesterimide described in Example 7.

A polyesterimide precursor was polymerized in the same manner used in Example 6, except that 4-aminophenyl-4'-aminobenzoate (hereinafter referred to as "APAB") was used, instead of PDA, as the diamine component, after which the polyesterimide precursor was made into film form and imidized to produce a polyesterimide film, and the physical properties of the film were evaluated in the same manner. The values of physical properties are shown in Table 1. In addition to the extremely low water absorption coefficient (0.38%) not heretofore achievable, the film also exhibited low linear heat expansion coefficient, high thermal stability, relatively low dielectric constant, and sufficient film toughness. The infrared absorption spectra of obtained thin films of polyesterimide precursor and polyesterimide are shown in FIGS. 15 and 16, respectively.

Example 8

Figure 17:
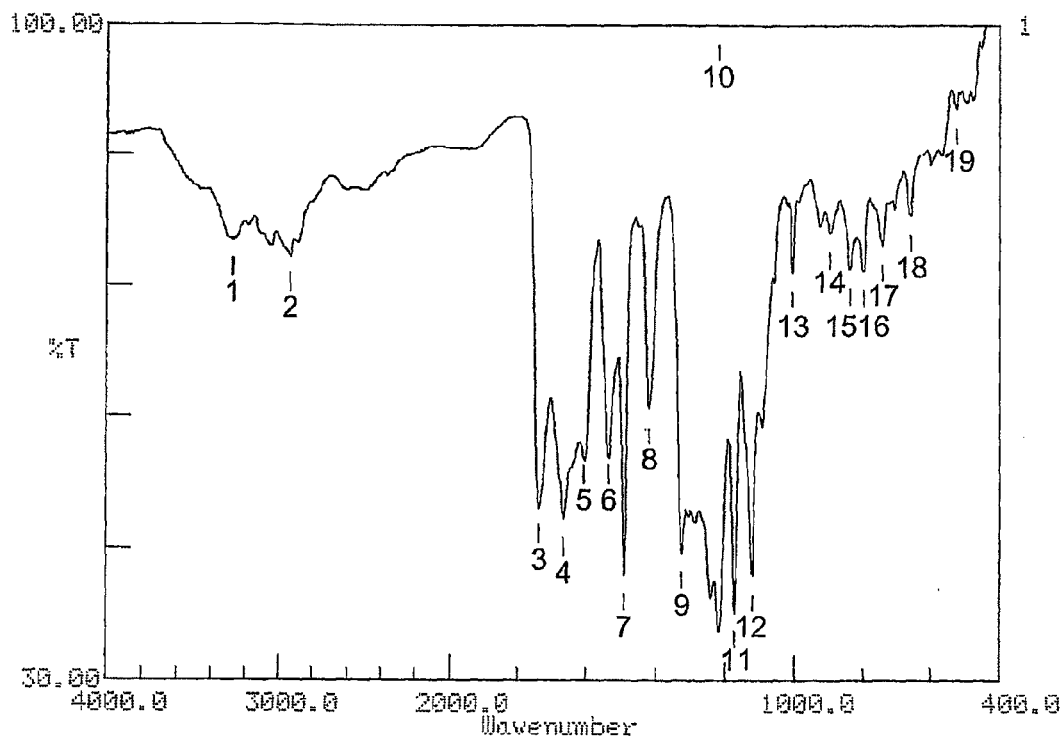
[FIG. 17] Infrared absorption spectrum of a thin film of the polyesterimide precursor described in Example 8.
Figure 18:
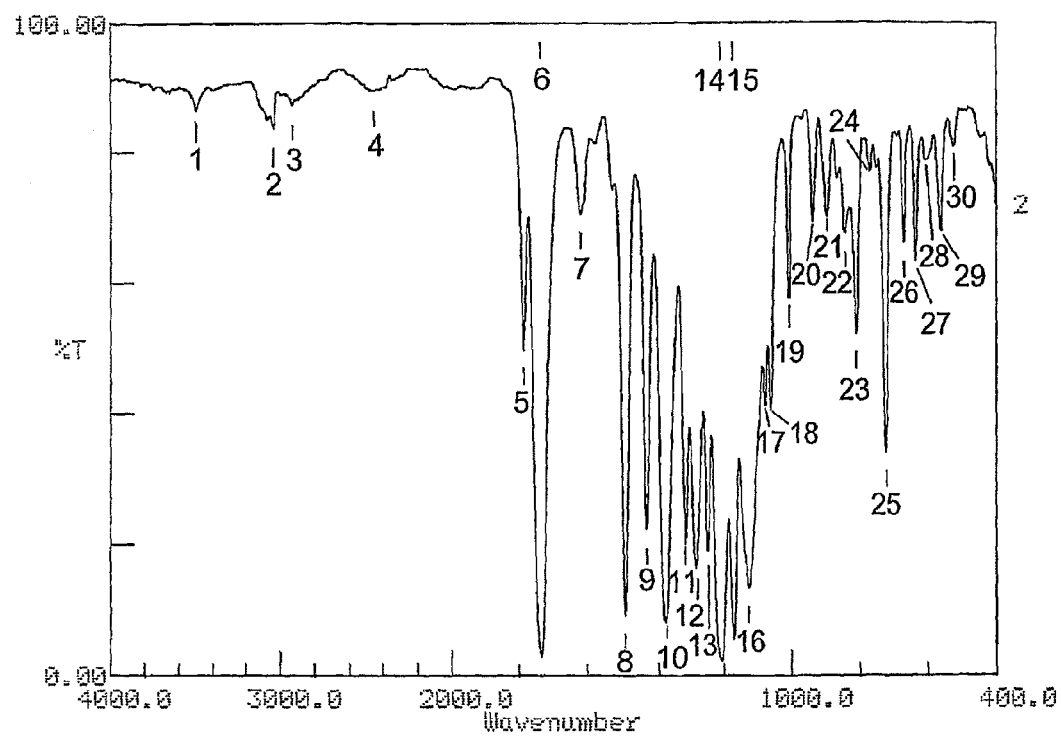
[FIG. 18] Infrared absorption spectrum of a thin film of the polyesterimide described in Example 8.

A polyesterimide precursor was polymerized in the same manner used in Example 6, except that 2,2'-bis (trifluoromethyl) benzidine (hereinafter referred to as "TFMB") was used, instead of PDA, as the diamine component, after which the polyesterimide precursor was made into film form and imidized to produce a polyesterimide film, and the physical properties of the film were evaluated in the same manner. The values of physical properties are shown in Table 1. The film exhibited relatively low linear heat expansion coefficient, extremely low water absorption coefficient, high thermal stability, relatively low dielectric constant, and sufficient film toughness. The infrared absorption spectra of obtained thin films of polyesterimide precursor and polyesterimide are shown in FIGS. 17 and 18, respectively.

Example 9

Figure 19:
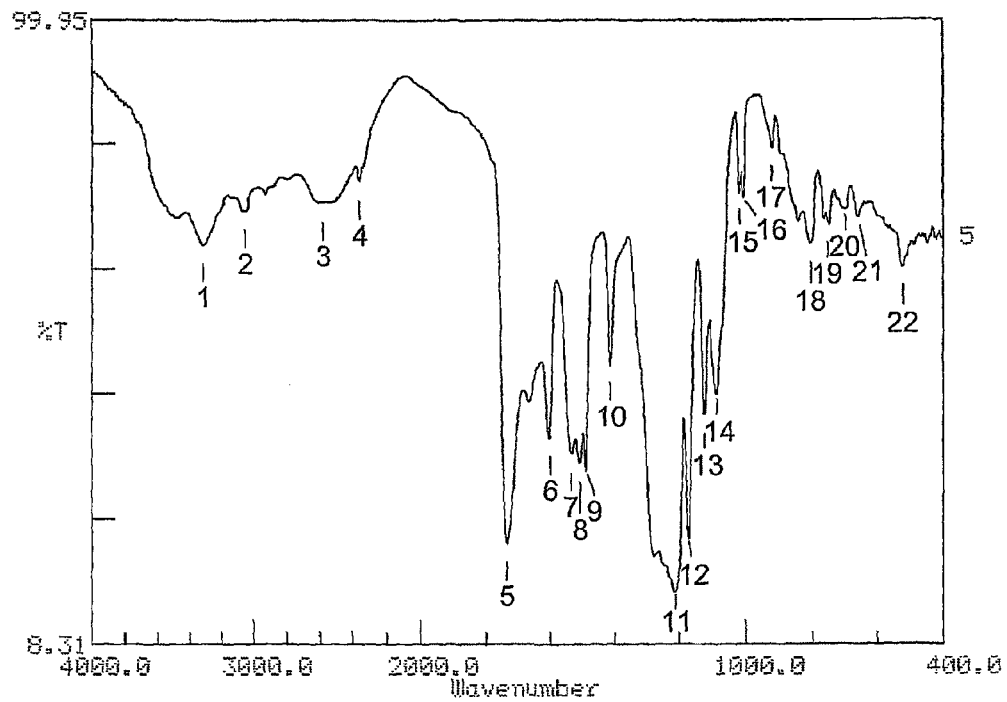
[FIG. 19] Infrared absorption spectrum of a thin film of the polyesterimide precursor described in Example 9.
Figure 20:
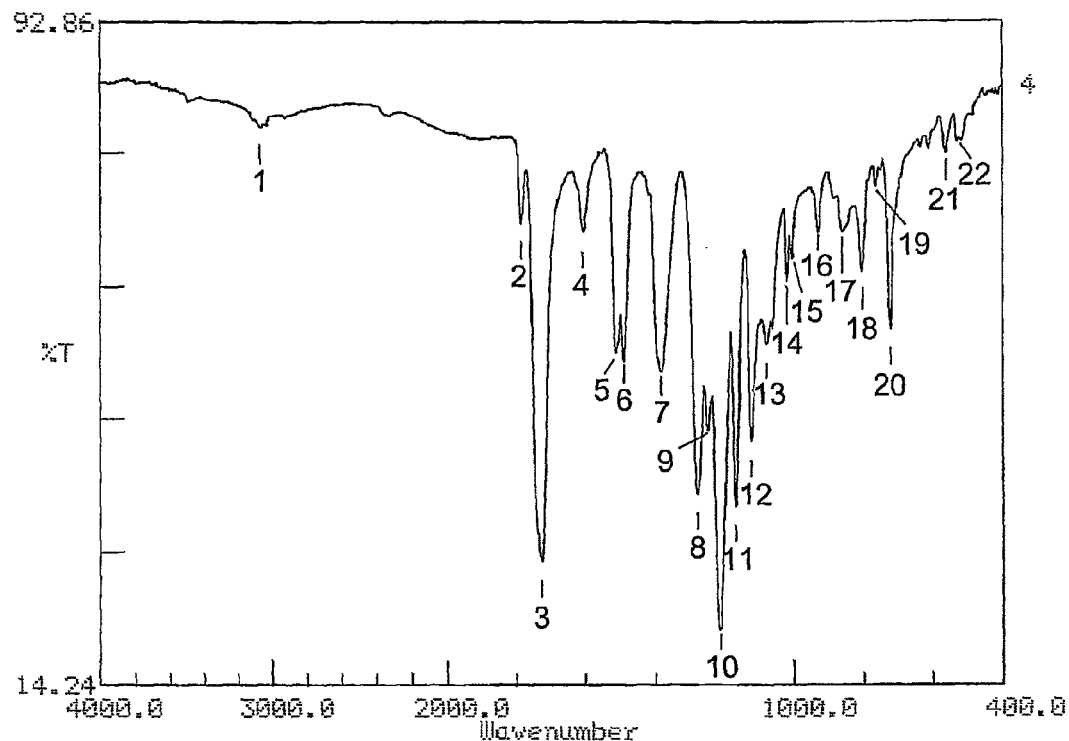
[FIG. 20] Infrared absorption spectrum of a thin film of the polyesterimide described in Example 9.

A copolymer of polyesterimide precursor was polymerized in the same manner used in Example 6, except that APAB and 4,4'-oxydianiline (hereinafter referred to as "ODA") were used in combination, instead of PDA, as the diamine component, after which the copolymer was made into film form and imidized to produce a polyesterimide film, and the physical properties of the film were evaluated in the same manner. The mol ratio of APAB and ODA used was 85:15. The values of physical properties are shown in Table 1. The film exhibited low linear heat expansion coefficient, extremely low water absorption coefficient, high thermal stability, relatively low dielectric constant, and sufficient film toughness. The infrared absorption spectra of obtained thin films of polyesterimide precursor and polyesterimide are shown in FIGS. 19 and 20, respectively.

Example 10

Figure 21:
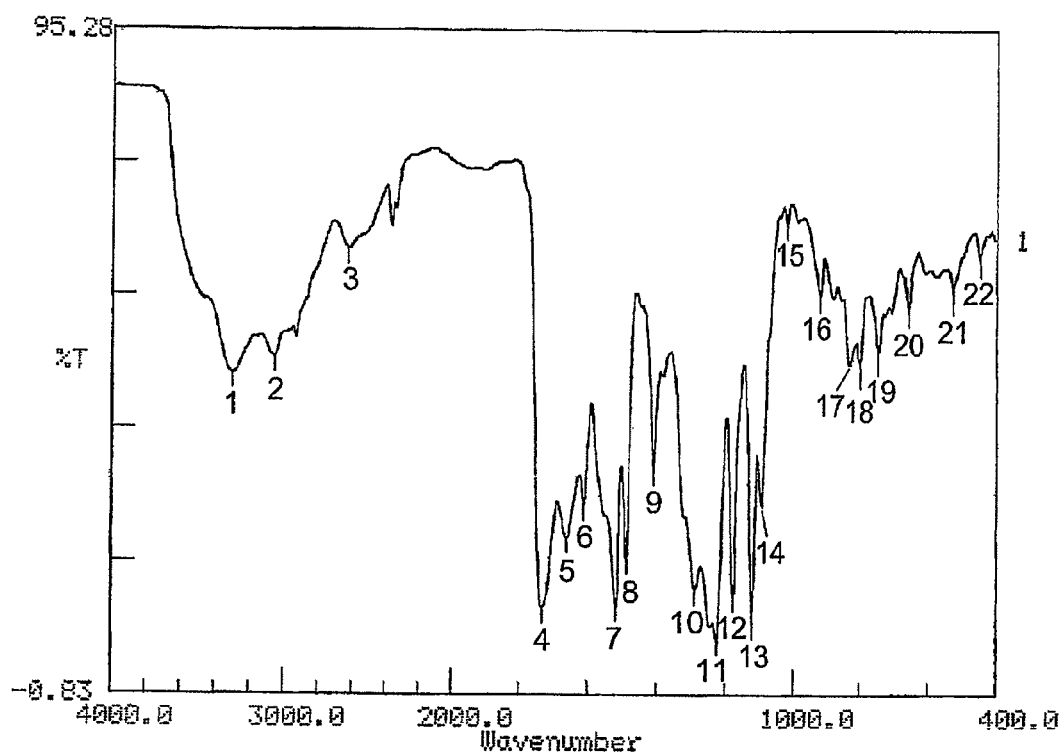
[FIG. 21] Infrared absorption spectrum of a thin film of the polyesterimide precursor described in Example 10.
Figure 22:
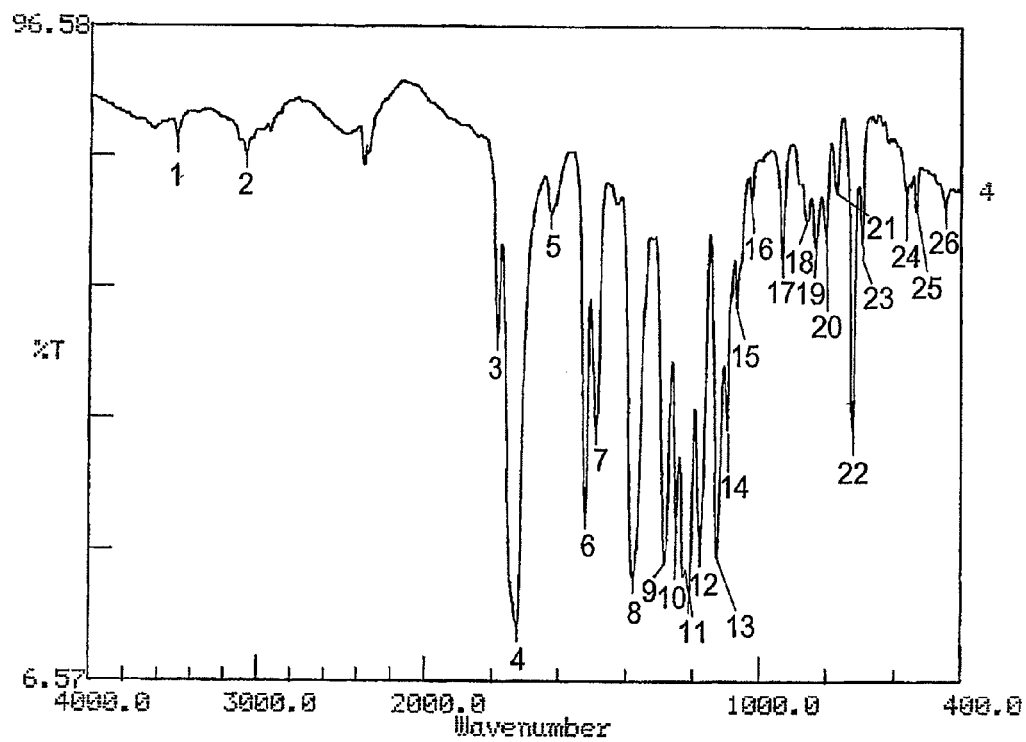
[FIG. 22] Infrared absorption spectrum of a thin film of the polyesterimide described in Example 10.

A polyesterimide precursor was polymerized in the same manner used in Example 6, except that the compound expressed by formula (16) and obtained in Example 2 was used, instead of the compound expressed by formula (21), as the ester group-containing tetracarboxylic acid dianhydride, after which the polyesterimide precursor was made into film form and imidized to produce a polyesterimide film, and the physical properties of the film were evaluated in the same manner. The values of physical properties are shown in Table 1. The film exhibited excellent physical properties similar to the polyesterimide described in Example 6. The infrared absorption spectra of thin films of polyesterimide precursor and polyesterimide are shown in FIGS. 21 and 22, respectively.

Example 11

Figure 23:
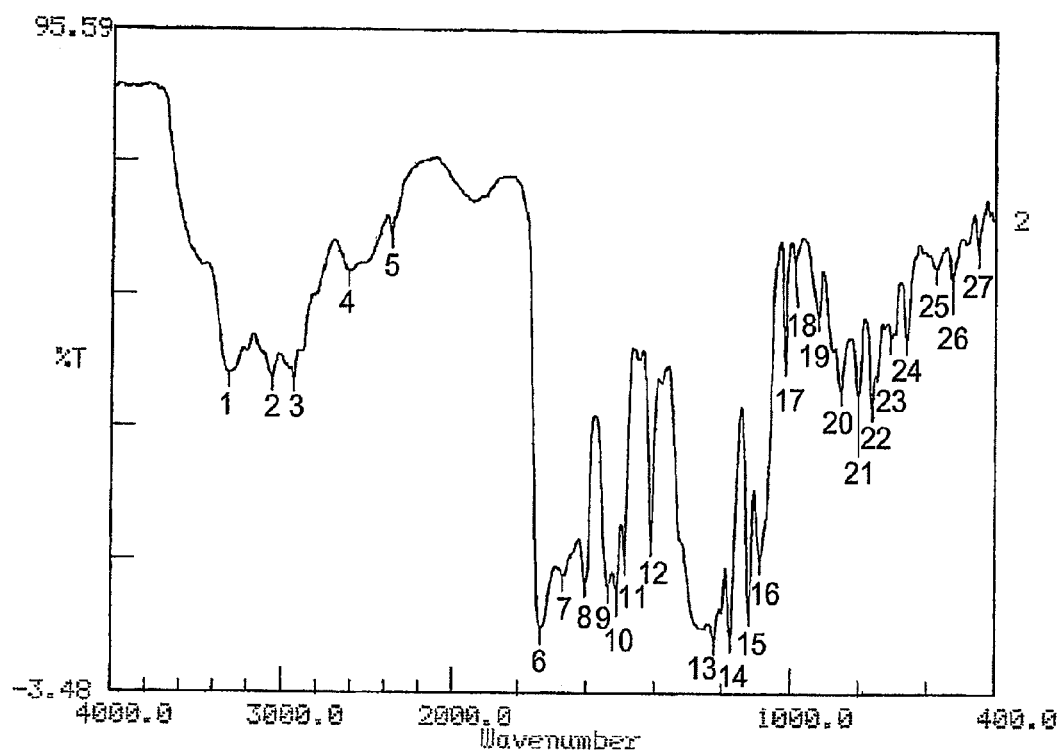
[FIG. 23] Infrared absorption spectrum of a thin film of the polyesterimide precursor described in Example 11.
Figure 24:
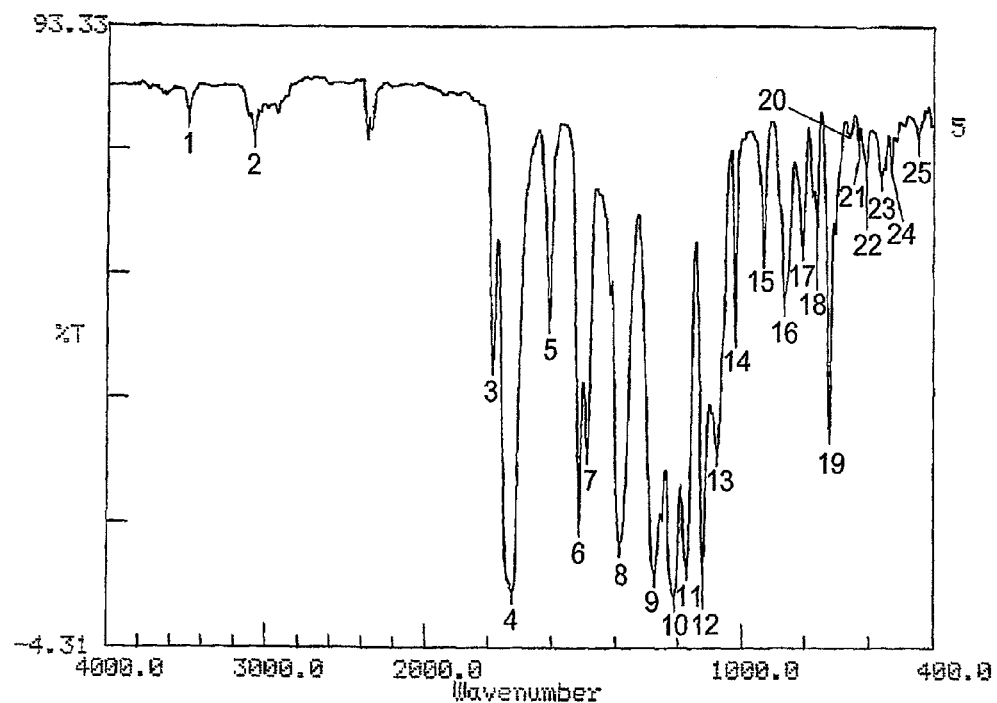
[FIG. 24] Infrared absorption spectrum of a thin film of the polyesterimide described in Example 11.

A polyesterimide precursor was polymerized in the same manner used in Example 6, except that APAB was used, instead of PDA, as the diamine component and that the compound expressed by formula (16) and obtained in Example 2 was used, instead of the compound expressed by formula (21), as the ester group-containing tetracarboxylic acid dianhydride, after which the polyesterimide precursor was made into film form and imidized to produce a polyesterimide film, and the physical properties of the film were evaluated in the same manner. The values of physical properties are shown in Table 1. The film exhibited excellent physical properties similar to the polyesterimide described in Example 7. The infrared absorption spectra of thin films of polyesterimide precursor and polyesterimide are shown in FIGS. 23 and 24, respectively.

Example 12

Figure 25:
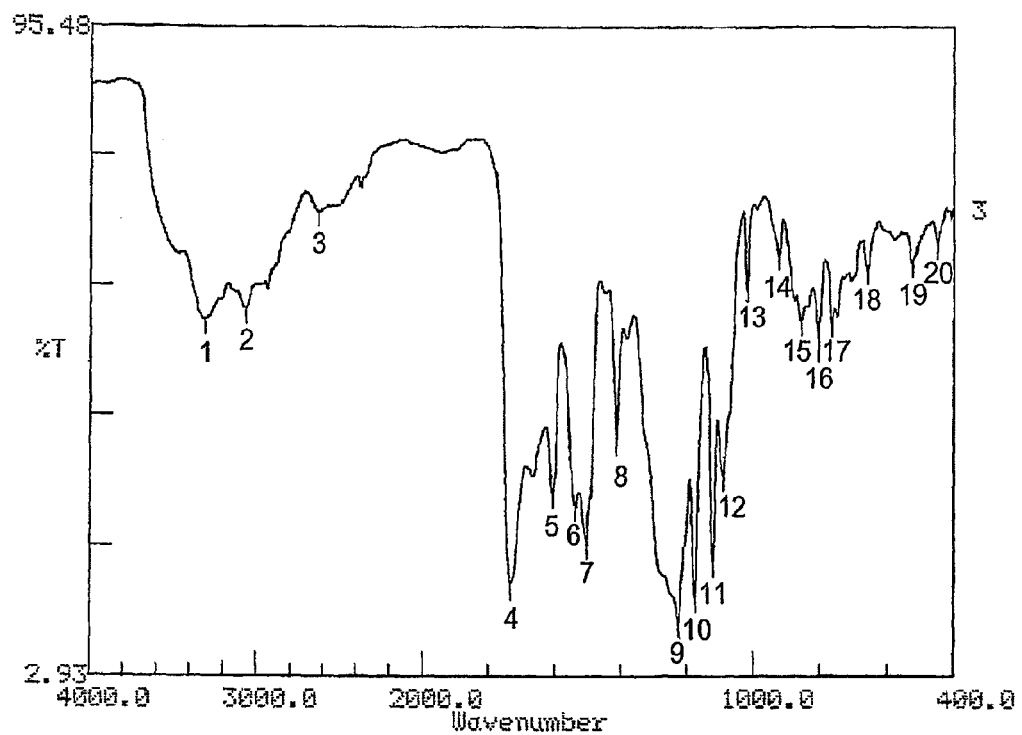
[FIG. 25] Infrared absorption spectrum of a thin film of the polyesterimide precursor described in Example 12.
Figure 26:
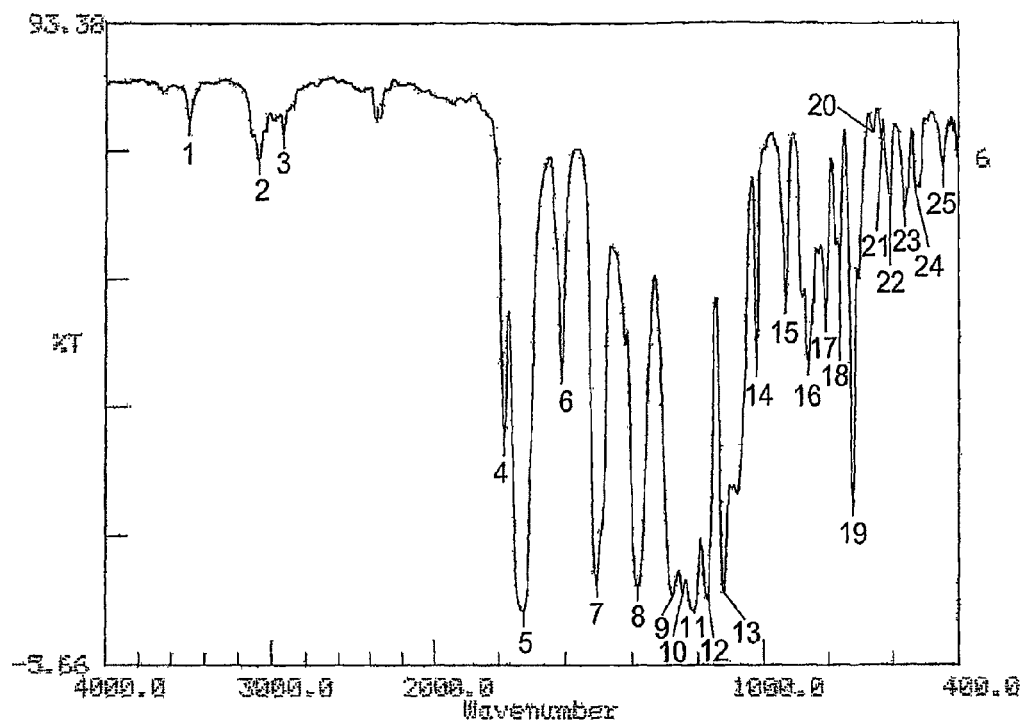
[FIG. 26] Infrared absorption spectrum of a thin film of the polyesterimide described in Example 12.

A polyesterimide precursor was polymerized in the same manner used in Example 6, except that APAB and ODA were used in combination, instead of PDA, as the diamine component and that the compound expressed by formula (16) and obtained in Example 2 was used, instead of the compound expressed by formula (21), as the ester group-containing tetracarboxylic acid dianhydride. The mol ratio of APAB and ODA was 70:30. Thereafter, the polyesterimide precursor was made into film form and imidized in the same manner used in Example 6 to produce a polyesterimide film, and the physical properties of the film were evaluated in the same manner. The values of physical properties are shown in Table 1. The film exhibited excellent physical properties similar to other polyesterimides described above. The infrared absorption spectra of thin films of polyesterimide precursor and polyesterimide are shown in FIGS. 25 and 26, respectively.

Example 13

Figure 27:
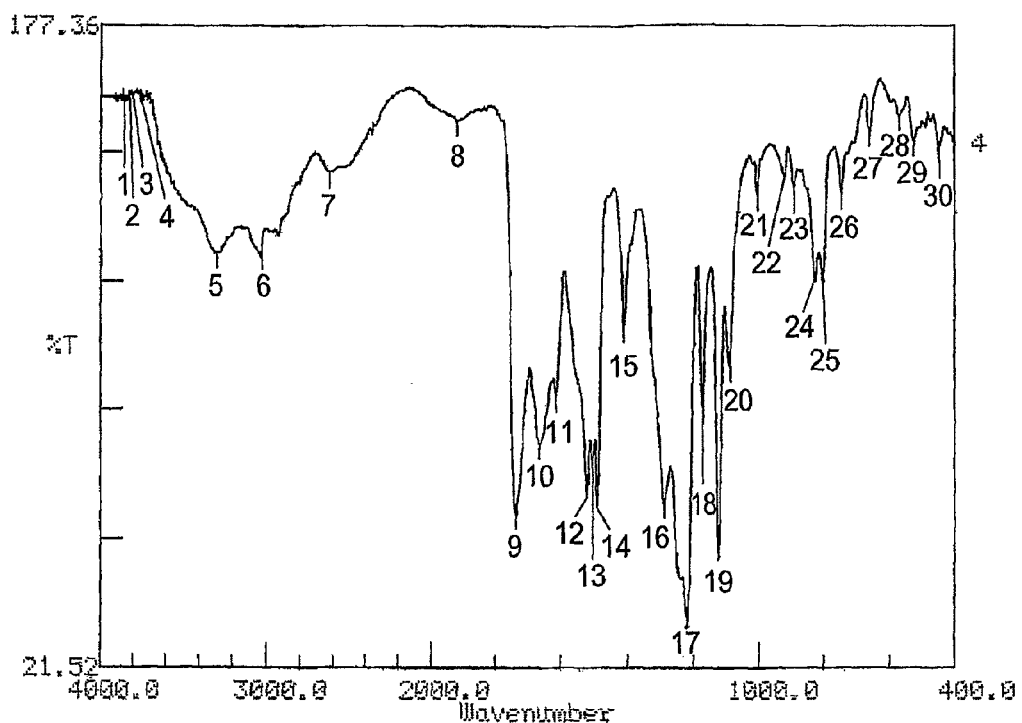
[FIG. 27] Infrared absorption spectrum of a thin film of the polyesterimide precursor described in Example 13.
Figure 28:
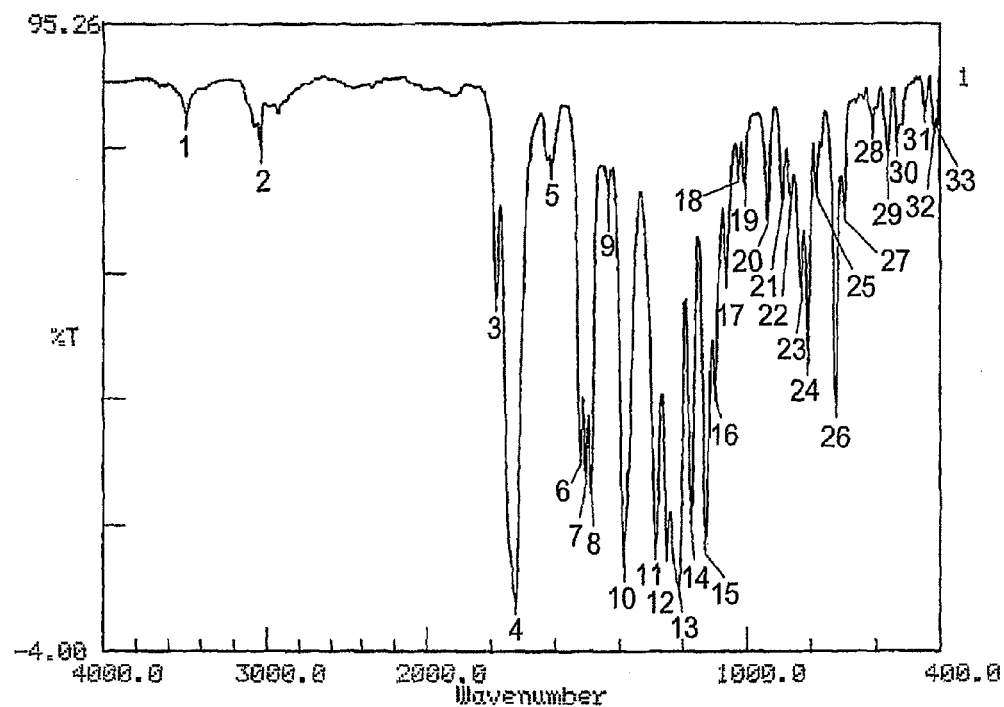
[FIG. 28] Infrared absorption spectrum of a thin film of the polyesterimide described in Example 13.

A polyesterimide precursor was polymerized in the same manner used in Example 6, except that PDA and ODA were used in combination, instead of PDA, as the diamine component and that the compound expressed by formula (24) and obtained in Example 5 was used, instead of the compound expressed by formula (21), as the ester group-containing tetracarboxylic acid dianhydride. The mol ratio of PDA and ODA was 70:30. Thereafter, the polyesterimide precursor was made into film form and imidized in the same manner used in Example 6 to produce a polyesterimide film, and the physical properties of the film were evaluated in the same manner. The values of physical properties are shown in Table 1. The film exhibited excellent physical properties similar to other polyesterimides described above. The infrared absorption spectra of thin films of polyesterimide precursor and polyesterimide are shown in FIGS. 27 and 28, respectively.

Example 14

Figure 29:
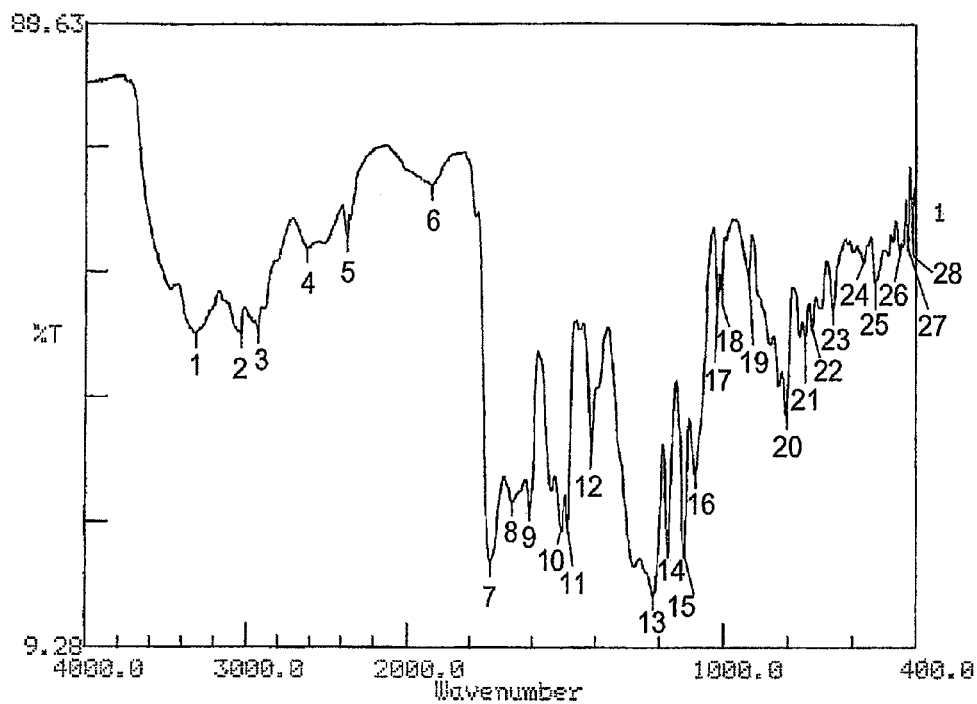
[FIG. 29] Infrared absorption spectrum of a thin film of the polyesterimide precursor described in Example 14.
Figure 30:
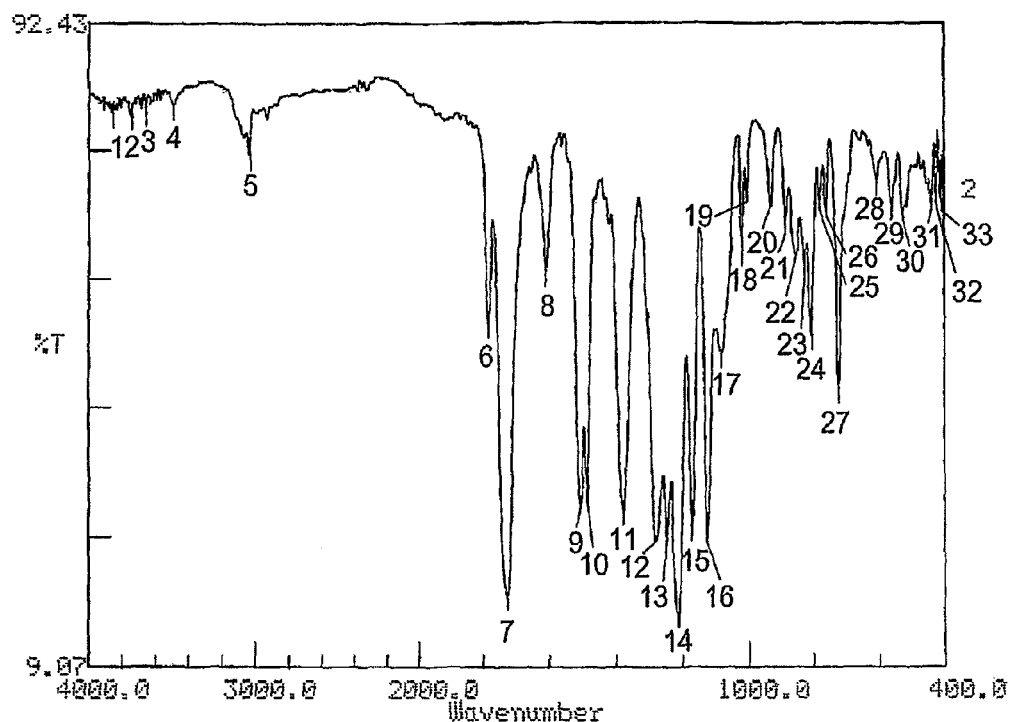
[FIG. 30] Infrared absorption spectrum of a thin film of the polyesterimide described in Example 14.

A polyesterimide precursor was polymerized in the same manner used in Example 6, except that APAB and ODA were used in combination, instead of PDA, as the diamine component and that the compound expressed by formula (24) and obtained in Example 5 was used, instead of the compound expressed by formula (21), as the ester group-containing tetracarboxylic acid dianhydride. The mol ratio of APAB and ODA was 70:30. Thereafter, the polyesterimide precursor was made into film form and imidized in the same manner used in Example 6 to produce a polyesterimide film, and the physical properties of the film were evaluated in the same manner. The values of physical properties are shown in Table 1. The film exhibited excellent physical properties similar to other polyesterimides described above. The infrared absorption spectra of thin films of polyesterimide precursor and polyesterimide are shown in FIGS. 29 and 30, respectively.

Comparative Example 1

A polyesterimide precursor was polymerized in the same manner used in Example 6, except that a tetracarboxylic acid dianhydride expressed by formula (4) was used, instead of the compound expressed by formula (21), as the ester group-containing tetracarboxylic acid dianhydride, after which the polyesterimide precursor was made into film form and imidized to produce a polyesterimide film, and the physical properties of the film were evaluated in the same manner. The water absorption coefficient of the film was higher than the values of other polyesterimide films conforming to the present invention. This is because this film had a lower content of the phenylene group functioning as a hydrophobic group.

TABLE 1

| | [η] (dL/g) | CTE (ppm/K) | Tg (°C.) | Water absorption coefficient (%) | $Td^5N_2$ (°C.) | $Td^5air$ (°C.) | Young's modulus (GPa) | Breaking elongation (%) | Breaking strength (GPa) | Birefringence | ε cal | CHE (ppm/RH %) |
|---|---|---|---|---|---|---|---|---|---|---|---|---|
| Example 6 | 1.72 | 7.3 | 438 | 0.88 | 479 | 451 | 7.66 | 3.6 | | 0.17 | 3.25 | |
| Example 7 | 0.75 | 12.1 | 396 | 0.38 | 467 | 440 | 6.18 | 7.5 | | 0.16 | 3.31 | |
| Example 8 | 1.19 | 28.1 | 350 | 0.26 | 473 | 459 | 4.76 | 26.1 | | 0.17 | 3.14 | |
| Example 9 | 1.00 | 18.8 | 378 | 0.43 | 466 | 442 | 5.61 | 26.4 | | 0.16 | 3.30 | 4.0 |
| Example 10 | 1.64 | 4.8 | 386 | 0.71 | 474 | 464 | 6.21 | 7.3 | 0.197 | 0.118 | 3.06 | |
| Example 11 | 2.14 | 5.0 | 376 | 0.23 | 459 | 452 | 5.58 | 7.5 | 0.190 | 0.115 | 3.01 | 0.64 |
| Example 12 | 0.99 | 26.6 | 350 | | | | | | | 0.116 | 3.09 | 1.48 |
| Example 13 | 1.26 | 10.7 | 392 | 0.51 | 481 | 456 | 5.21 | 11.5 | 0.207 | 0.080 | 3.05 | |
| Example 14 | 0.66 | 29.1 | 378 | 0.26 | 483 | 448 | 4.40 | 17.7 | 0.166 | | | |
| Comparative Example 1 | 5.19 | 3.2 | ND | 1.60 | 481 | 463 | 8.86 | 5.4 | | 0.22 | 3.22 | |

ND: Not detectable in dynamic viscoelasticity measurement (measurement range: room temperature to 450° C.)

What is claimed is:

1. A polyesterimide having a repeating unit expressed by formula (3-2):

(3-2)

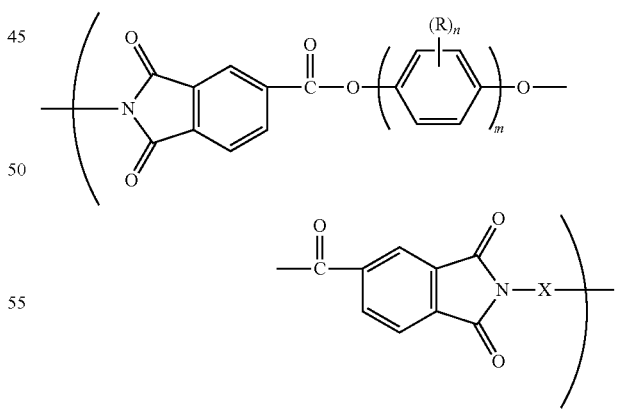

wherein each R is independent and represents a straight or branched-chain alkyl group with 1 to 6 carbon atoms or straight or branched-chain alkoxyl group with 1 to 6 carbon atoms, n is an integer of 0 to 4, m is an integer of 3 or 4, and X represents a bivalent aromatic group and/or aliphatic group.

* * * * *

UNITED STATES PATENT AND TRADEMARK OFFICE
CERTIFICATE OF CORRECTION

| | |
|---|---|
| PATENT NO. | : 9,023,974 B2 |
| APPLICATION NO. | : 12/523856 |
| DATED | : May 5, 2015 |
| INVENTOR(S) | : Masatoshi Hasegawa |

Page 1 of 1

It is certified that error appears in the above-identified patent and that said Letters Patent is hereby corrected as shown below:

Specification

In column 3 at line 8 (approx.), Change "-pateint" to -- -patent--.

In column 3 at line 9 (approx.), Change "2,for" to --2, for--.

In column 21 at line 32, Change "hexafluoropropanic" to --hexafluoropropanoic--.

In column 21 at line 33, Change "propanic" to --propanoic--.

In column 21 at line 38, Change "-dioxotetrahydrofurane-" to -- -dioxotetrahydrofuran- --.

In column 21 at line 40, Change "tetrahydrofurane-" to --tetrahydrofuran- --.

Claims

In column 32 at lines 62-64 (approx.), In Claim 1, after "carbon" delete "expressed by formula (21), as the ester group-containing tetracarboxylic acid dianhydride. The mol ratio of PDA and".

Signed and Sealed this
Twenty-eighth Day of June, 2016

Michelle K. Lee
*Director of the United States Patent and Trademark Office*